United States Patent
Curley

(10) Patent No.: US 9,730,748 B2
(45) Date of Patent: Aug. 15, 2017

(54) DEVICES AND METHODS FOR SHAPING THERAPY IN FLUID ENHANCED ABLATION

(71) Applicant: Thermedical, Inc., Waltham, MA (US)

(72) Inventor: Michael G. Curley, Weston, MA (US)

(73) Assignee: Thermedical, Inc., Waltham, MA (US)

(*) Notice: Subject to any disclaimer, the term of this patent is extended or adjusted under 35 U.S.C. 154(b) by 330 days.

(21) Appl. No.: 14/202,425

(22) Filed: Mar. 10, 2014

(65) Prior Publication Data

US 2014/0188106 A1    Jul. 3, 2014

Related U.S. Application Data

(60) Division of application No. 13/445,365, filed on Apr. 12, 2012, now Pat. No. 8,702,697, which is a (Continued)

(51) Int. Cl.
*A61B 18/14* (2006.01)
*A61B 18/04* (2006.01)
(Continued)

(52) U.S. Cl.
CPC ............ *A61B 18/04* (2013.01); *A61B 18/082* (2013.01); *A61B 18/1477* (2013.01);
(Continued)

(58) Field of Classification Search
CPC .. A61B 2018/1472; A61B 2018/00791; A61B 2018/00029; A61B 2018/00011;
(Continued)

(56) References Cited

U.S. PATENT DOCUMENTS 4,160,455 A    7/1979  Law
4,424,190 A    1/1984  Mather, III et al.
(Continued)

FOREIGN PATENT DOCUMENTS

CN    1119127 C    8/2003
CN    1897885 A    1/2007
(Continued)

OTHER PUBLICATIONS

Chinese Office Action for Application No. 201280028621.X, issued Jul. 31, 2015 (18 pages).
(Continued)

*Primary Examiner* — Michael Peffley
(74) *Attorney, Agent, or Firm* — Nutter McClennen & Fish LLP

(57) ABSTRACT

Devices and methods for shaping an ablation treatment volume formed in fluid enhanced ablation therapy are provided. The devices and methods disclosed herein utilize the interaction of fluids to create ablation treatment volumes having a variety of shapes. In one embodiment, a method for forming an ablation treatment volume having a desired shape includes delivering therapeutic energy to tissue to form an ablation treatment volume and simultaneously delivering a first fluid and a second fluid to the tissue. The first and second fluids can convect the therapeutic energy in a desired direction such that the ablation treatment volume has a desired shape.

19 Claims, 12 Drawing Sheets

Related U.S. Application Data continuation of application No. 13/445,034, filed on Apr. 12, 2012, and a continuation of application No. 13/445,036, filed on Apr. 12, 2012, now Pat. No. 9,138,287, and a continuation of application No. 13/445,373, filed on Apr. 12, 2012, now Pat. No. 9,445,861, and a continuation of application No. 13/445,040, filed on Apr. 12, 2012, now Pat. No. 8,945,121.

(60) Provisional application No. 61/474,574, filed on Apr. 12, 2011.

(51) Int. Cl.
*A61B 18/08* (2006.01)
*A61B 18/00* (2006.01)
*A61B 17/00* (2006.01)

(52) U.S. Cl.
CPC .......... *A61B 2017/00526* (2013.01); *A61B 2018/00029* (2013.01); *A61B 2018/00577* (2013.01); *A61B 2018/00642* (2013.01); *A61B 2018/00773* (2013.01); *A61B 2018/00791* (2013.01); *A61B 2018/00797* (2013.01); *A61B 2018/00809* (2013.01); *A61B 2018/00821* (2013.01); *A61B 2018/046* (2013.01); *A61B 2018/1425* (2013.01); *F04C 2270/041* (2013.01); *Y10T 29/49016* (2015.01); *Y10T 29/49085* (2015.01)

(58) Field of Classification Search
CPC .... A61B 18/1492; A61B 18/14; A61B 18/082
See application file for complete search history.

(56) References Cited

U.S. PATENT DOCUMENTS

| | | | |
|---|---|---|---|
| 5,271,413 A | 12/1993 | Dalamagas et al. | |
| 5,336,222 A | 8/1994 | Durgin, Jr. et al. | |
| 5,403,311 A | 4/1995 | Abele et al. | |
| 5,409,487 A | 4/1995 | Jalbert et al. | |
| 5,431,648 A | 7/1995 | Lev | |
| 5,431,649 A | 7/1995 | Mulier et al. | |
| 5,449,380 A | 9/1995 | Chin | |
| 5,456,682 A | 10/1995 | Edwards et al. | |
| 5,458,597 A * | 10/1995 | Edwards | A61N 5/045 604/21 |
| 5,462,521 A | 10/1995 | Brucker et al. | |
| 5,472,441 A | 12/1995 | Edwards et al. | |
| 5,496,271 A | 3/1996 | Burton et al. | |
| 5,522,815 A | 6/1996 | Durgin, Jr. et al. | |
| 5,545,195 A | 8/1996 | Lennox et al. | |
| 5,549,559 A | 8/1996 | Eshel | |
| 5,653,692 A | 8/1997 | Masterson et al. | |
| 5,728,143 A | 3/1998 | Gough et al. | |
| 5,735,846 A | 4/1998 | Panescu et al. | |
| 5,800,482 A | 9/1998 | Pomeranz et al. | |
| 5,827,269 A | 10/1998 | Saadat | |
| 5,891,094 A | 4/1999 | Masterson et al. | |
| 5,891,134 A | 4/1999 | Goble et al. | |
| 5,954,719 A | 9/1999 | Chen et al. | |
| 5,964,791 A | 10/1999 | Bolmsjo | |
| 6,024,743 A | 2/2000 | Edwards | |
| 6,030,379 A | 2/2000 | Panescu et al. | |
| 6,032,077 A | 2/2000 | Pomeranz | |
| 6,045,549 A | 4/2000 | Smethers et al. | |
| 6,056,746 A | 5/2000 | Goble et al. | |
| 6,071,280 A * | 6/2000 | Edwards | A61B 18/1477 606/41 |
| 6,112,123 A | 8/2000 | Kelleher et al. | |
| 6,119,041 A | 9/2000 | Pomeranz et al. | |
| 6,139,570 A | 10/2000 | Saadat et al. | |
| 6,139,571 A | 10/2000 | Fuller et al. | |
| 6,179,803 B1 | 1/2001 | Edwards et al. | |
| 6,208,881 B1 | 3/2001 | Champeau | |
| 6,233,490 B1 | 5/2001 | Kasevich | |
| 6,238,393 B1 * | 5/2001 | Mulier | A61B 18/1482 606/41 |
| 6,272,370 B1 | 8/2001 | Gillies et al. | |
| 6,302,904 B1 | 10/2001 | Wallsten et al. | |
| 6,315,777 B1 * | 11/2001 | Comben | A61B 18/1477 606/41 |
| 6,328,735 B1 * | 12/2001 | Curley | A61B 18/04 606/14 |
| 6,337,994 B1 | 1/2002 | Stoianovici et al. | |
| 6,358,273 B1 | 3/2002 | Strul et al. | |
| 6,405,067 B1 | 6/2002 | Mest et al. | |
| 6,409,722 B1 * | 6/2002 | Hoey | A61N 7/022 128/898 |
| 6,443,947 B1 | 9/2002 | Marko et al. | |
| 6,463,332 B1 | 10/2002 | Aldrich | |
| 6,464,694 B1 | 10/2002 | Massengill | |
| 6,468,274 B1 | 10/2002 | Alleyne et al. | |
| 6,475,213 B1 * | 11/2002 | Whayne | A61B 18/1492 600/374 |
| 6,477,396 B1 | 11/2002 | Mest et al. | |
| 6,494,902 B2 * | 12/2002 | Hoey | A61B 18/1206 128/898 |
| 6,529,756 B1 | 3/2003 | Phan et al. | |
| 6,564,096 B2 | 5/2003 | Mest | |
| 6,565,561 B1 | 5/2003 | Goble et al. | |
| 6,603,997 B2 | 8/2003 | Doody | |
| 6,620,155 B2 | 9/2003 | Underwood et al. | |
| 6,641,580 B1 | 11/2003 | Sharkey et al. | |
| 6,669,685 B1 | 12/2003 | Rizoiu et al. | |
| 6,678,552 B2 | 1/2004 | Pearlman | |
| 6,702,810 B2 | 3/2004 | McClurken et al. | |
| 6,752,802 B1 | 6/2004 | Isenberg et al. | |
| 6,772,012 B2 | 8/2004 | Woloszko et al. | |
| 6,814,730 B2 | 11/2004 | Li | |
| 6,904,303 B2 | 6/2005 | Phan et al. | |
| 6,972,014 B2 | 12/2005 | Eum et al. | |
| 7,001,378 B2 | 2/2006 | Yon et al. | |
| 7,070,597 B2 | 7/2006 | Truckai et al. | |
| 7,101,369 B2 | 9/2006 | van der Welde | |
| 7,160,259 B2 | 1/2007 | Tardy et al. | |
| 7,179,256 B2 | 2/2007 | Mest | |
| 7,207,989 B2 | 4/2007 | Pike, Jr. et al. | |
| 7,244,254 B2 | 7/2007 | Brace et al. | |
| 7,270,659 B2 | 9/2007 | Ricart et al. | |
| 7,311,703 B2 | 12/2007 | Turovskiy et al. | |
| 7,387,625 B2 | 6/2008 | Hovda et al. | |
| 7,387,630 B2 | 6/2008 | Mest | |
| 7,412,273 B2 | 8/2008 | Jais et al. | |
| 7,416,552 B2 * | 8/2008 | Paul | A61B 18/1492 606/41 |
| 7,559,905 B2 | 7/2009 | Kagosaki et al. | |
| 7,604,634 B2 | 10/2009 | Hooven | |
| 7,879,030 B2 | 2/2011 | Paul et al. | |
| 7,938,822 B1 | 5/2011 | Berzak et al. | |
| 7,951,143 B2 | 5/2011 | Wang et al. | |
| 7,993,335 B2 | 8/2011 | Rioux et al. | |
| 8,128,620 B2 | 3/2012 | Wang et al. | |
| 8,128,621 B2 | 3/2012 | Wang et al. | |
| 8,273,082 B2 | 9/2012 | Wang et al. | |
| 8,287,531 B2 | 10/2012 | Mest | |
| 8,333,762 B2 | 12/2012 | Mest et al. | |
| 8,369,922 B2 | 2/2013 | Paul et al. | |
| 8,439,907 B2 | 5/2013 | Auth et al. | |
| 8,444,638 B2 * | 5/2013 | Woloszko | A61B 18/042 606/32 |
| 8,449,535 B2 | 5/2013 | Deno et al. | |
| 8,591,507 B2 | 11/2013 | Kramer et al. | |
| 8,663,226 B2 | 3/2014 | Germain | |
| 8,700,133 B2 | 4/2014 | Hann | |
| 8,702,697 B2 | 4/2014 | Curley | |
| 8,755,860 B2 | 6/2014 | Paul et al. | |
| 8,758,349 B2 | 6/2014 | Germain et al. | |
| 8,864,760 B2 | 10/2014 | Kramer et al. | |
| 8,945,121 B2 | 2/2015 | Curley | |
| 9,033,972 B2 | 5/2015 | Curley | |

(56) References Cited

U.S. PATENT DOCUMENTS

| | | |
|---|---|---|
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 2001/0031946 A1 | 10/2001 | Walker et al. |
| 2002/0120259 A1 | 8/2002 | Lettice et al. |
| 2002/0123749 A1 | 9/2002 | Jain |
| 2002/0183735 A1 | 12/2002 | Edwards et al. |
| 2003/0109871 A1 | 6/2003 | Johnson et al. |
| 2003/0120271 A1 | 6/2003 | Burnside et al. |
| 2004/0006336 A1 | 1/2004 | Swanson |
| 2004/0116922 A1 | 6/2004 | Hovda et al. |
| 2004/0220559 A1 | 11/2004 | Kramer et al. |
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0165391 A1 | 7/2005 | Maguire et al. |
| 2005/0187599 A1 | 8/2005 | Sharkey et al. |
| 2005/0192652 A1 | 9/2005 | Cioanta et al. |
| 2005/0245923 A1 | 11/2005 | Christopherson et al. |
| 2005/0267552 A1 | 12/2005 | Conquergood et al. |
| 2006/0085054 A1 | 4/2006 | Zikorus et al. |
| 2006/0118127 A1 | 6/2006 | Chinn |
| 2006/0216275 A1 | 9/2006 | Mon |
| 2006/0259024 A1 | 11/2006 | Turovskiy et al. |
| 2006/0276780 A1 | 12/2006 | Brace et al. |
| 2006/0287650 A1 | 12/2006 | Cao et al. |
| 2007/0032786 A1 | 2/2007 | Francischelli |
| 2007/0185483 A1 | 8/2007 | Butty et al. |
| 2007/0219434 A1 | 9/2007 | Abreu |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0161788 A1 | 7/2008 | Dando et al. |
| 2008/0161797 A1 | 7/2008 | Wang et al. |
| 2008/0167650 A1 | 7/2008 | Joshi et al. |
| 2008/0275440 A1 | 11/2008 | Kratoska et al. |
| 2008/0288038 A1 | 11/2008 | Paul et al. |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1 | 7/2009 | Luttich |
| 2009/0254083 A1 | 10/2009 | Wallace et al. |
| 2010/0030098 A1 | 2/2010 | Fojtik |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2012/0108938 A1 | 5/2012 | Kauphusman et al. |
| 2012/0130381 A1 | 5/2012 | Germain |
| 2012/0265190 A1 | 10/2012 | Curley et al. |
| 2012/0265199 A1 | 10/2012 | Curley |
| 2012/0265200 A1 | 10/2012 | Curley |
| 2012/0265276 A1 | 10/2012 | Curley |
| 2012/0277737 A1 | 11/2012 | Curley |
| 2012/0310230 A1 | 12/2012 | Willis |
| 2014/0052117 A1 | 2/2014 | Curley |
| 2014/0188106 A1 | 7/2014 | Curley |
| 2014/0275977 A1 | 9/2014 | Curley et al. |
| 2014/0276743 A1 | 9/2014 | Curley |
| 2014/0350542 A1 | 11/2014 | Kramer et al. |
| 2015/0066025 A1 | 3/2015 | Curley |
| 2015/0223882 A1 | 8/2015 | Curley |
| 2015/0351823 A1 | 12/2015 | Curley |
| 2015/0359582 A1 | 12/2015 | Curley et al. |

FOREIGN PATENT DOCUMENTS

| | | |
|---|---|---|
| CN | 101578073 A | 11/2009 |
| CN | 101999931 A | 4/2011 |
| EP | 0 895 756 A1 | 2/1999 |
| EP | 0 908 156 A1 | 4/1999 |
| EP | 1 033 107 A1 | 9/2000 |
| EP | 2 042 112 A2 | 4/2009 |
| EP | 2 430 996 A2 | 3/2012 |
| JP | 10-505268 A | 5/1998 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/32186 A1 | 7/1999 |
| WO | 2005/048858 A1 | 6/2005 |
| WO | 2005/089663 A1 | 9/2005 |
| WO | 2006/055658 A1 | 5/2006 |
| WO | 2006/095171 A1 | 9/2006 |
| WO | 2006/102471 A2 | 9/2006 |
| WO | 2006/103951 A1 | 10/2006 |
| WO | 2007/080578 A2 | 7/2007 |
| WO | 2010/002733 A1 | 1/2010 |
| WO | 2010/151619 A2 | 12/2010 |
| WO | 2012/071058 A1 | 5/2012 |

OTHER PUBLICATIONS

Japanese Office Action for Application No. 2014-505263, mailed Jan. 26, 2016 (4 pages).
Chinese Office Action for Application No. 201280028609.9, issued May 27, 2015. (22 pages).
Chinese Office Action for Application No. 201280028620.5, issued May 27, 2015. (26 pages).
Brace CL. Microwave tissue ablation: biophysics, technology, and applications.; Crit Rev Biomed Eng. 2010;38 (1):65-78.
David R. Lide (ed)., CRC Handbook of Chemistry and Physics, 87th Edition. 2006. p. 8-81. CRC Press, Florida.
International Search Report and Written Opinion for Application No. PCT/US2012/033203, issued Sep. 21, 2012. (23 pages).
International Search Report and Written Opinion for Application No. PCT/US2012/033213, issued Sep. 21, 2012. (17 pages).
International Search Report and Written Opinion for Application No. PCT/US2012/033216, issued Sep. 21, 2012. (17 pages).
International Search Report and Written Opinion for Application No. PCT/US2012/033327, issued Sep. 21, 2012. (14 pages).
International Search Report and Written Opinion for Application No. PCT/US2012/033332, issued Sep. 21, 2012. (20 pages).
International Search Report and Written Opinion for Application No. PCT/US2013/053977, issued Nov. 14, 2012. (20 pages).
Nath et al., Prog. Card. Dis. 37(4):185-205 (1995).
Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.
Sapareto et al., Int. J Rad. One. Biol. Phys. 10(6):787-800 (1984).
International Search Report and Written Opinion for Application No. PCT/US2014/024731, mailed Jul. 21, 2014 (39 pages).
Extended Search Report and Written Opinion for EP 12 77 0537 dated Oct. 10, 2014 (6 pages).
Extended Search Report and Written Opinion for EP 12 77 0631.5 dated Oct. 1, 2014 (6 Pages).
Extended Search Report and Written Opinion for EP 12 77 1331.1 dated Sep. 25, 2014 (6 Pages).
Extended Search Report and Written Opinion for EP 12 77 1876 dated Oct. 13, 2014 (6 pages).
Chinese Office Action for Application No. 201280028611.6, issued Jul. 29, 2015. (23 pages).

(56) References Cited

OTHER PUBLICATIONS

Extended European Search Report and Written Opinion for Application No. 12771601.7 issued Oct. 27, 2014 (7 pages).
Extended European Search Report and Search Opinion for Application No. 13829821.1 issued Mar. 17, 2016 (7 pages).
Japanese Office Action for Application No. 2014-505266, mailed Feb. 23, 2016 (7 pages).
Young, S.T., et al., An instrument using variation of resistance to aid in needle tip insertion in epidural block in monkeys. Med Instrum. Oct. 1987;21(5):266-8. Abstract Only.

* cited by examiner

DEVICES AND METHODS FOR SHAPING THERAPY IN FLUID ENHANCED ABLATION

RELATED APPLICATIONS

This application is a divisional application of U.S. application Ser. No. 13/445,365, filed on Apr. 12, 2012, now issued as U.S. Pat. No. 8,702,697, entitled "Devices and Methods for Shaping Therapy in Fluid Enhanced Ablation, which claims priority to U.S. Provisional Application Ser. No. 61/474,574, filed on Apr. 12, 2011, entitled "Improvement in Ablation Catheters. " This application is also a continuation application of U.S. application Ser. No. 13/445,034, filed Apr. 12, 2012, entitled "Devices and Methods for Remote Temperature Monitoring in Fluid Enhanced Ablation Therapy," U.S. application Ser. No. 13/445,036, filed Apr. 12, 2012, now issued as U.S. Pat. No. 9,138,287, entitled "Methods and Devices for Heating Fluid in Fluid Enhanced Ablation Therapy," U.S. application Ser. No. 13/445,373, filed Apr. 12, 2012, now issued as U.S. Pat. No. 9,445,861, entitled "Methods and Devices for Controlling Ablation Therapy," and U.S. application Ser. No. 13/445,040, filed Apr. 12, 2012, now issued as U.S. Pat. No. 8,945,121, entitled "Methods and Devices for Use of Degassed Fluids with Fluid Enhanced Ablation Devices." The disclosures of each of these applications are hereby incorporated by reference in their entirety.

FIELD

The present invention relates generally to fluid enhanced ablation, such as the SERF™ ablation technique (Saline Enhanced Radio Frequency™ ablation). More particularly, this invention relates to devices and methods for controlling the shape of a treatment zone created during fluid enhanced ablation.

BACKGROUND

The use of thermal energy to destroy bodily tissue can be applied to a variety of therapeutic procedures, including the destruction of tumors. Thermal energy can be imparted to the tissue using various forms of energy, such as radio frequency electrical energy, microwave or light wave electromagnetic energy, or ultrasonic vibrational energy. Radio frequency (RF) ablation, for example, can be effected by placing one or more electrodes against or into tissue to be treated and passing high frequency electrical current into the tissue. The current can flow between closely spaced emitting electrodes or between an emitting electrode and a larger, common electrode located remotely from the tissue to be heated.

One disadvantage with these techniques is that maximum heating often occurs at or near the interface between the therapeutic tool and the tissue. In RF ablation, for example, the maximum heating can occur in the tissue immediately adjacent to the emitting electrode. This can reduce the conductivity of the tissue, and in some cases, can cause water within the tissue to boil and become water vapor. As this process continues, the impedance of the tissue can increase and prevent current from entering into the surrounding tissue. Thus, conventional RF instruments are limited in the volume of tissue that can be treated.

Fluid enhanced ablation therapy, such as the SERF ablation technique (Saline Enhanced Radio Frequency™ ablation), can treat a greater volume of tissue than conventional RF ablation. The SERF ablation technique is described in U.S. Pat. No. 6,328,735, which is hereby incorporated by reference. Using the SERF ablation technique, saline is passed through a needle and heated, and the heated fluid is delivered to the tissue immediately surrounding the needle. The saline helps distribute the heat developed adjacent to the needle and thereby allows a greater volume of tissue to be treated with a therapeutic dose of ablative energy. The therapy is usually completed once a target volume of tissue reaches a desired therapeutic temperature, or otherwise receives a therapeutic dose of energy.

Fluid enhanced ablation therapy generally creates a spherically-shaped treatment zone in tissue surrounding an ablation device. In some situations, however, it can be desirable to create a treatment zone having a non-spherical shape. For example, some lesions or tumors suitable for treatment with fluid enhanced ablation are not spherical in shape. In addition, it can be desirable to protect certain structures, such as sensitive nerve cells, located very near to a lesion or other target volume of tissue.

In still other situations, it can be desirable to introduce directionality into a treatment zone created using ablation therapy. For example, a common treatment for cardiac dysrhythmias, such as atrial fibrillation, involves a catheter-based procedure that selectively ablates tissue in the atrial walls in order to create defined pathways for the passage of the electrical signals that drive heartbeats. Current methods of ablation therapy, however, cannot create treatment zones similar to these directional pathways in the ventricle because they cannot heat through the ventricle wall, so this technique cannot be applied to the treatment of ventricular tachycardia. Fluid enhanced ablation is capable of heating through the ventricle wall, but the ablation zones created are so large that it is not possible to create pathways for the electrical signals, as too much of the heart is ablated.

Accordingly, there remains a need for improved devices and methods for shaping a treatment zone created during fluid enhanced ablation therapy.

SUMMARY

The present invention generally provides devices and methods for improving ablation therapy by controlling the shape of the treatment zone. In one aspect of the invention, a method for forming an ablation treatment volume in tissue having a desired shape is provided that includes delivering therapeutic energy to tissue to form an ablation treatment volume in the tissue, and simultaneously delivering a first fluid and a second fluid to the tissue, the first and second fluids convecting the therapeutic energy in a desired direction such that the ablation treatment volume has a desired shape.

In some embodiments, the method can further include delivering additional fluids to the tissue in combination with the first fluid and the second fluid. For example, a third, fourth, fifth, etc. fluid can be introduced in some embodiments. Each of these fluids can be introduced into the tissue such that they interact to form an ablation treatment volume of a desired shape. Any number of fluids can be utilized.

In some embodiments, the first and second fluids can be delivered at different temperatures. A number of different temperatures can be selected for the first and second fluids. In some embodiments, the first fluid can be at about 50° C. In other embodiments, the second fluid can be at about 37° C. However, any temperature can be selected for either the first or the second fluid. Further, the method can be used in a variety of locations within a patient's body. In certain embodiments, for example, the tissue can be in the heart. In other embodiments, the tissue can be in the liver. In still other embodiments, the tissue can be any of the prostate, uterus, kidney, lung, breast, or any other organ or tissue within a patient's body.

In certain embodiments, the first and second fluids can be delivered through one or more elongate bodies inserted into the tissue. In addition, the method can include a variety of other steps for facilitating the shaping of the ablation treatment volume. For example, the method can further include adjusting any of a fluid flow rate and a fluid temperature for any of the first fluid and the second fluid to further shape the ablation treatment volume. Similarly, the method can also include adjusting a level of therapeutic energy delivered to the tissue to further shape the ablation treatment volume. In some embodiments, delivering therapeutic energy to tissue can include activating an ablation element configured to transmit electrical energy into the tissue. Still further, in other embodiments, the method can further include repeating the steps of delivering therapeutic energy and simultaneously delivering a first and a second fluid in a plurality of locations to form a treatment volume having an elongate planar shape.

In some embodiments, the first fluid can be delivered from first and second opposed longitudinal portions of an inner lumen of an elongate body, and the second fluid can be delivered from third and fourth opposed longitudinal portions of the inner lumen. In addition, the third and fourth portions can be radially offset from the first and second portions.

In still other embodiments, delivering the first fluid can include ejecting the first fluid from at least one outlet port formed in a proximal portion of a sidewall of an elongate member, and delivering the second fluid can include ejecting the second fluid from at least one outlet port formed in a distal portion of a sidewall of an elongate member adjacent to the proximal portion.

In still other embodiments, the method can include removing the first and second fluids from the tissue so as to further shape the ablation treatment volume. The first and second fluids can be selectively removed using, for example, an elongate body configured to draw fluid from tissue surrounding the elongate body.

In another aspect of the invention, a method for shaping therapeutic energy delivered to tissue is provided that includes positioning a first elongate body in a patient's body at a first location, where the first elongate body has an inner lumen extending therethrough, at least one outlet port formed therein, at least one ablation element disposed along a length thereof, and at least one heater element disposed within the inner lumen. The method further includes positioning a second elongate body in a patient's body at a second location, where the second elongate body has an inner lumen extending therethrough and at least one outlet port formed therein. The method further includes simultaneously delivering a first fluid from the first elongate body and a second fluid from the second elongate body such that the first and second fluids interact to shape an ablation treatment volume.

The method can have a variety of modifications, all of which are considered within the scope of the invention. In some embodiments, for example, the first fluid and the second fluid can be at different temperatures. In other embodiments, the method can further include delivering therapeutic energy from the ablation element disposed along the first elongate body. In such an embodiment, the interaction of the fluid can direct the energy from the ablation element to shape the volume of tissue that receives therapeutic energy.

In other embodiments, positioning the first elongate body at a first location and positioning the second elongate body at a second location can include positioning in a patient's body an elongate member having the first and second elongate bodies disposed thereon. The elongate member can be, for example, a catheter or other elongate shaft or member, as discussed below. Further, in some embodiments, the second elongate body can be positioned at a location adjacent to a structure to be protected from therapeutic energy, such as a cluster of nerve cells.

In another aspect of the invention, an ablation device is provided that includes an elongate body having proximal and distal ends, an inner lumen extending through the elongate body, and at least two outlet ports formed in the elongate body configured to deliver fluid to tissue surrounding the elongate body. The elongate body also includes at least one ablation element disposed along a distal portion of the elongate body, the ablation element being configured to heat tissue surrounding the ablation element when the elongate body is inserted into tissue. Further, the at least two outlet ports are configured to deliver fluid at different temperatures.

The ablation device can have a variety of configurations and additional features. In some embodiments, the ablation device can further include at least one heater element associated with one or more of the two outlet ports, the at least one heater element being disposed within the inner lumen and configured to heat fluid flowing to the one or more associated outlet ports.

In other embodiments, the ablation device can further include at least one dividing member disposed within the inner lumen and configured to divide the inner lumen into two or more portions not in fluid communication with each other. Further, each portion can be in communication with one or more of the at least two outlet ports. In certain embodiments, the at least one dividing member can divide the inner lumen into four portions extending longitudinally along the inner lumen so as to divide the inner lumen into quadrants having opposed pairs. A heater element can be disposed within each portion of the first opposing pair of quadrants that is configured to heat fluid flowing therethrough to a first temperature. Further, a heater element can be disposed within each portion of the second opposing pair of quadrants that is configured to heat fluid flowing therethrough to a second temperature that is less than the first temperature. In still other embodiments, the at least one dividing member can divide the inner lumen into a proximal portion and a distal portion wherein each portion is associated with a different ablation element. The at least one dividing member can also include at least two dividing members that further divide the inner lumen to create a third portion that is proximal or distal to the distal portion. In certain embodiments, the device can also include two or more temperature sensors, and each temperature sensor can be disposed in a different portion of the inner lumen.

In another aspect of the invention, an ablation device is provided having an elongate member that has a distal end configured for introduction into a patient's body. The device also includes at least two elongate bodies disposed on the distal end of the elongate member. Each of the elongate bodies includes proximal and distal ends, an inner lumen extending therethrough, and at least one outlet port formed in the elongate body and configured to deliver fluid to tissue surrounding the elongate body. At least one of the elongate bodies includes at least one ablation element disposed along a distal portion of the elongate body and the ablation element is configured to heat tissue surrounding the ablation element. Further, at least one of the elongate bodies includes a heater element disposed within the inner lumen of the elongate body and the heater element is configured to heat fluid flowing through the inner lumen.

In some embodiments, the at least two elongate bodies can include first, second, and third elongate bodies arranged around the distal end of the elongate member a distance away from a longitudinal axis of the elongate member. For example, the first, second, and third elongate bodies can be arranged such that they are angularly offset from each other and positioned at a particular radius from the longitudinal axis of the elongate member. In other embodiments, the first, second, and third elongate bodies can be positioned in a straight line on the distal end of the elongate member. In such an embodiment, one or more of the elongate bodies can include an ablation element thereon.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Figure 1:
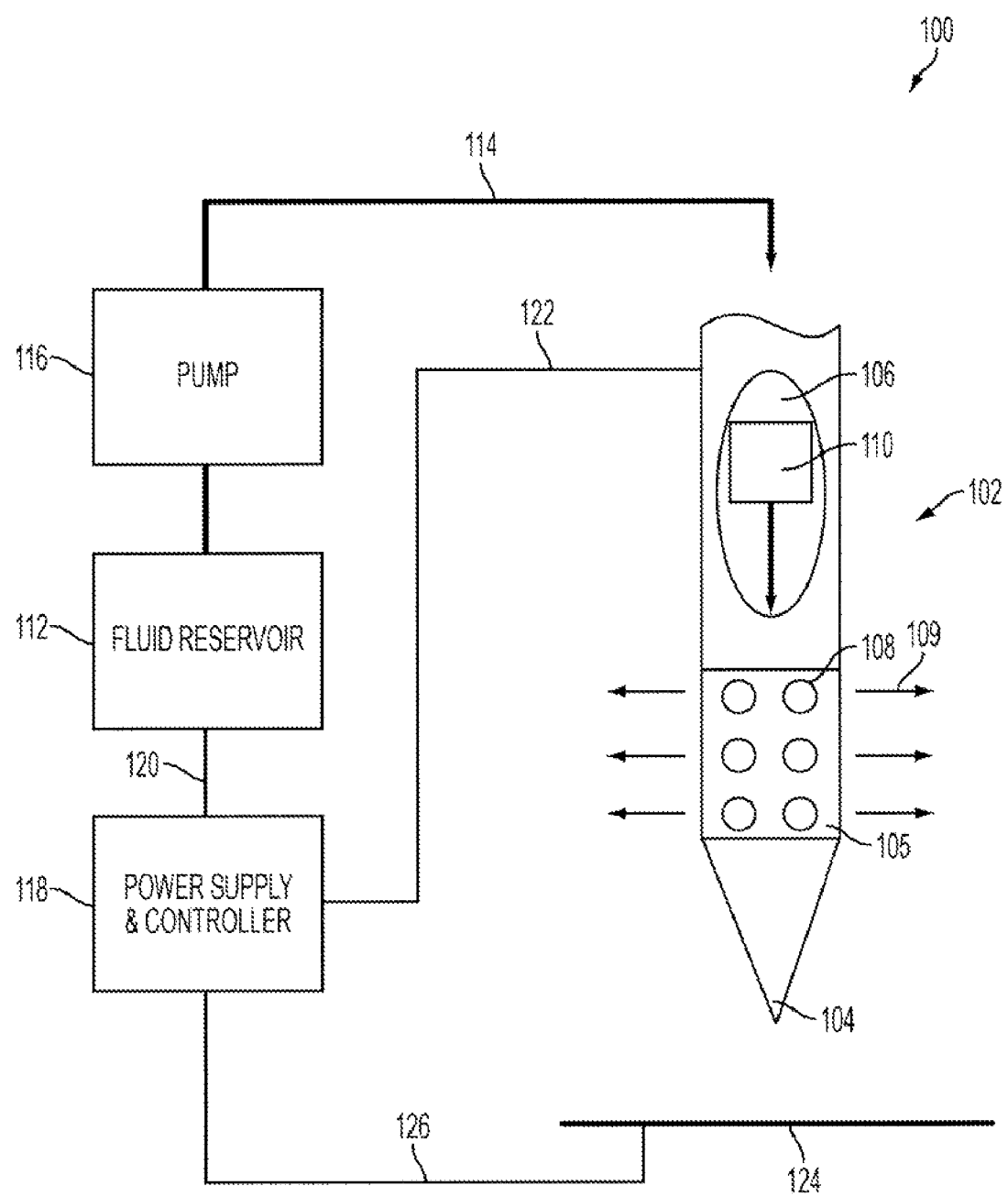
FIG. 1 is a diagram of one embodiment of a fluid enhanced ablation system.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. The terms "about" and "approximately" used for any numerical values or ranges indicate a suitable dimensional tolerance that allows the composition, part, or collection of elements to function for its intended purpose as described herein. These terms generally indicate a ±10% variation about a central value. Components described herein as being directly coupled may be directly coupled, or they may be indirectly coupled via one or more intermediate components. The recitation of any ranges of values herein is merely intended to serve as a shorthand method of referring individually to each separate value falling within the range, unless otherwise indicated herein, and each separate value is incorporated into the specification as if it were individually recited. Further, to the extent that linear or circular dimensions are used in the description of the disclosed devices, systems, and methods, such dimensions are not intended to limit the types of shapes that can be used in conjunction with such devices, systems, and methods. A person skilled in the art will recognize that an equivalent to such linear and circular dimensions can easily be determined for any geometric shape.

All methods described herein can be performed in any suitable order unless otherwise indicated herein or otherwise clearly contradicted by context. The use of any and all examples, or exemplary language (e.g., "such as"), provided herein is intended merely to better illuminate the invention and does not impose a limitation on the scope of the invention unless otherwise claimed. No language in the specification should be construed as indicating any non-claimed element as essential to the practice of the invention. Further, to the extent the term "saline" is used in conjunction with any embodiment herein, such embodiment is not limited to use of "saline" as opposed to another fluid unless explicitly indicated. Other fluids can typically be used in a similar manner.

Fluid Enhanced Ablation Systems

The present invention is generally directed to devices and methods for shaping a therapy or treatment zone or region created using fluid enhanced ablation. Fluid enhanced ablation, as mentioned above, is defined by passing a fluid into tissue while delivering therapeutic energy from an ablation element. The delivery of therapeutic energy into tissue can cause hyperthermia in the tissue, ultimately resulting in necrosis. This temperature-induced selective destruction of tissue can be utilized to treat a variety of conditions including tumors, fibroids, cardiac dysrhythmias (e.g., ventricular tachycardia, etc.), and others.

Fluid enhanced ablation, such as the SERF™ ablation technique (Saline Enhanced Radio Frequency™ ablation) described in U.S. Pat. No. 6,328,735 and incorporated by reference above, delivers fluid heated to a therapeutic temperature into tissue along with ablative energy. Delivering heated fluid enhances the ablation treatment because the fluid flow through the extracellular space of the treatment tissue can increase the heat transfer through the tissue by more than a factor of twenty. The flowing heated fluid therefore convects thermal energy from the ablation energy source further into the target tissue. In addition, the fact that the fluid is heated to a therapeutic temperature increases the amount of energy that can be imparted into the tissue. Finally, the fluid can also serve to constantly hydrate the tissue and prevent any charring and associated impedance rise.

Figure 2:
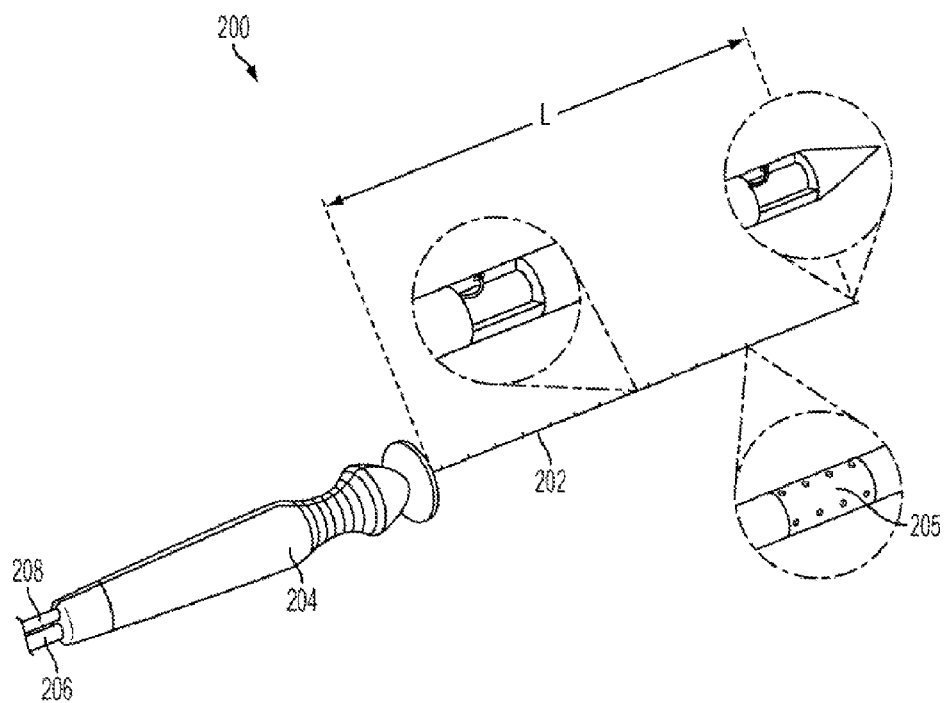
FIG. 2 is a perspective view of one embodiment of a medical device having an elongate body for use in fluid enhanced ablation.

FIG. 1 illustrates a diagram of one exemplary fluid ablation system 100. The system includes an elongate body 102 configured for insertion into a target volume of tissue. The elongate body can have a variety of shapes and sizes according to the geometry of the target tissue. Further, the particular size of the elongate body can depend on a variety of factors including the type and location of tissue to be treated, the size of the tissue volume to be treated, etc. By way of example only, in one embodiment, the elongate body can be a thin-walled stainless steel needle between about 16- and 18-gauge (i.e., an outer diameter of about 1.27 millimeters to about 1.65 millimeters), and having a length L (e.g., as shown in FIG. 2) that is approximately 25 cm. The elongate body 102 can include a pointed distal tip 104 configured to puncture tissue to facilitate introduction of the device into a target volume of tissue, however, in other embodiments the tip can be blunt and can have various other configurations. The elongate body 102 can be formed from a conductive material such that the elongate body can conduct electrical energy along its length to one or more ablation elements located along a distal portion of the elongate body. Emitter electrode 105 is an example of an ablation element capable of delivering RF energy from the elongate body.

In some embodiments, the emitter electrode 105 can be a portion of the elongate body 102. For example, the elongate body 102 can be coated in an insulating material along its entire length except for the portion representing the emitter electrode 105. More particularly, in one embodiment, the elongate body 102 can be coated in 1.5 mil of the fluoropolymer Xylan™ 8840. The electrode 105 can have a variety of lengths and shape configurations. In one embodiment, the electrode 105 can be a 4 mm section of a tubular elongate body that is exposed to surrounding tissue. Further, the electrode 105 can be located anywhere along the length of the elongate body 105 (and there can also be more than one electrode disposed along the length of the elongate body). In one embodiment, the electrode can be located adjacent to the distal tip 104. In other embodiments, the elongate body can be formed from an insulating material, and the electrode can be disposed around the elongate body or between portions of the elongate body.

In other embodiments, the electrode can be formed from a variety of other materials suitable for conducting current. Any metal or metal salt may be used. Aside from stainless steel, exemplary metals include platinum, gold, or silver, and exemplary metal salts include silver/silver chloride. In one embodiment, the electrode can be formed from silver/silver chloride. It is known that metal electrodes assume a voltage potential different from that of surrounding tissue and/or liquid. Passing a current through this voltage difference can result in energy dissipation at the electrode/tissue interface, which can exacerbate excessive heating of the tissue near the electrodes. One advantage of using a metal salt such as silver/silver chloride is that it has a high exchange current density. As a result, a large amount of current can be passed through such an electrode into tissue with only a small voltage drop, thereby minimizing energy dissipation at this interface. Thus, an electrode formed from a metal salt such as silver/silver chloride can reduce excessive energy generation at the tissue interface and thereby produce a more desirable therapeutic temperature profile, even where there is no liquid flow about the electrode.

The electrode 105 or other ablation element can include one or more outlet ports 108 that are configured to deliver fluid from an inner lumen 106 extending through the elongate body 102 into surrounding tissue (as shown by arrows 109). Alternatively, the electrode 105 can be positioned near one or more outlet ports 108 formed in the elongate body 102. In many embodiments, it can be desirable to position the electrode adjacent to the one or more outlet ports to maximize the effect of the flowing fluid on the therapy. The outlet ports 108 can be formed in a variety of sizes, numbers, and pattern configurations. In addition, the outlet ports 108 can be configured to direct fluid in a variety of directions with respect to the elongate body 102. These can include the normal orientation (i.e., perpendicular to the elongate body surface) shown by arrows 109 in FIG. 1, as well as orientations directed proximally and distally along a longitudinal axis of the elongate body 102, including various orientations that develop a circular or spiral flow of liquid around the elongate body. Still further, in some embodiments, the elongate body 102 can be formed with an open distal end that serves as an outlet port. By way of further example, in one embodiment, twenty-four equally-spaced outlet ports 108 having a diameter of about 0.4 mm can be created around the circumference of the electrode 105 using Electrical Discharge Machining (EDM). One skilled in the art will appreciate that additional manufacturing methods are available to create the outlet ports 108. In addition, in some embodiments, the outlet ports can be disposed along a portion of the elongate body adjacent to the electrode, rather than being disposed in the electrode itself.

The inner lumen 106 that communicates with the outlet ports 108 can also house a heating assembly 110 configured to heat fluid as it passes through the inner lumen 106 just prior to being introduced into tissue. Detailed discussion of various embodiments of the heating assembly 110 suitable for use in devices and methods of the present invention can be found in related U.S. application Ser. No. 13/445,036 entitled "Methods and Devices for Remote Temperature Monitoring in Fluid Enhanced Ablation Therapy," filed concurrently with the present application and incorporated by reference in its entirety above.

The portion of the elongate body located distal to the electrode 105 or other ablation element can be solid or filled such that the inner lumen 106 terminates at the distal end of the electrode 105. In one embodiment, the inner volume of the portion of the elongate body distal to the electrode can be filled with a plastic plug that can be epoxied in place or held by an interference fit. In other embodiments, the portion of the elongate body distal to the electrode can be formed from solid metal and attached to the proximal portion of the elongate body by welding, swaging, or any other technique known in the art.

Fluid can be supplied to the inner lumen 106 and heating assembly 110 from a fluid reservoir 112. The fluid reservoir 112 can be connected to the inner lumen 106 via a fluid conduit 114. The fluid conduit 114 can be, for example, a length of flexible plastic tubing. The fluid conduit 114 can also be a rigid tube, or a combination of rigid and flexible tubing.

Fluid can be urged from the fluid reservoir 112 into the inner lumen 106 by a pump 116. The pump 116 can be a syringe-type pump that produces a fixed volume flow with advancement of a plunger (not shown). An example of such a pump is a Model 74900 sold by Cole-Palmer Corporation of Chicago, Ill. Other types of pumps, such as a diaphragm pump, may also be employed.

The pump 116 can be controlled by a power supply and controller 118. The power supply and controller 118 can deliver electrical control signals to the pump 116 to cause the pump to produce a desired flow rate of fluid. The power supply and controller 118 can be connected to the pump 116 via an electrical connection 120. The power supply and controller 118 can also be electrically connected to the elongate body 102 via connection 122, and to a collector electrode 124 via connection 126. In addition, the power supply and controller 118 can be connected to the heating assembly 110 through a similar electrical connection.

The collector electrode 124 can have a variety of forms. For example, the collector electrode 124 can be a large electrode located outside a patient's body. In other embodiments, the collector electrode 124 can be a return electrode located elsewhere along the elongate body 102, or it can be located on a second elongate body introduced into a patient's body near the treatment site.

In operation, the power supply and controller 118 can drive the delivery of fluid into target tissue at a desired flow rate, the heating of the fluid to a desired therapeutic temperature, and the delivery of therapeutic ablative energy via the one or more ablation elements, such as electrode 105. To do so, the power supply and controller 118 can itself comprise a number of components for generating, regulating, and delivering required electrical control and therapeutic energy signals. For example, the power supply and controller 118 can include one or more frequency generators to create one or more RF signals of a given amplitude and frequency. These signals can be amplified by one or more RF power amplifiers into relatively high-voltage, high-amperage signals, e.g., 50 volts at 1 amp. These RF signals can be delivered to the ablation element via one or more electrical connections 122 and the elongate body 102 such that RF energy is passed between the emitter electrode 105 and the collector electrode 124 that can be located remotely on a patient's body. In embodiments in which the elongate body is formed from non-conductive material, the one or more electrical connections 122 can extend through the inner lumen of the elongate body or along its outer surface to deliver current to the emitter electrode 105. The passage of RF energy between the ablation element and the collector electrode 124 can heat the tissue surrounding the elongate body 102 due to the inherent electrical resistivity of the tissue. The power supply and controller 118 can also include a directional coupler to feed a portion of the one or more RF signals to, for example, a power monitor to permit adjustment of the RF signal power to a desired treatment level.

The elongate body 102 illustrated in FIG. 1 can be configured for insertion into a patient's body in a variety of manners. FIG. 2 illustrates one embodiment of a medical device 200 having an elongate body 202 disposed on a distal end thereof configured for laparoscopic or direct insertion into a target area of tissue. In addition to the elongate body 202, the device 200 can include a handle 204 to allow an operator to manipulate the device. The handle 204 can include one or more electrical connections 206 that connect various components of the elongate body (e.g., the heating assembly and ablation element 205) to, for example, the power supply and controller 118 described above. The handle 204 can also include at least one fluid conduit 208 for connecting a fluid source to the device 200.

While device 200 is one exemplary embodiment of a medical device that can be adapted for use in fluid enhanced ablation, a number of other devices can also be employed. For example, a very small elongate body can be required in treating cardiac dysrhythmias, such as ventricular tachycardia. In such a case, an appropriately sized elongate body can be, for example, disposed at a distal end of a catheter configured for insertion into the heart via the circulatory system. In one embodiment, a stainless steel needle body between about 20- and about 25-gauge (i.e., an outer diameter of about 0.5 millimeters to about 0.9 millimeters) can be disposed at a distal end of a catheter. The catheter can have a variety of sizes but, in some embodiments, it can have a length of about 120 cm and a diameter of about 8 French ("French" is a unit of measure used in the catheter industry to describe the size of a catheter and is equal to three times the diameter of the catheter in millimeters).

Therapeutic Treatment Using Fluid Enhanced Ablation

Ablation generally involves the application of high or low temperatures to cause the selective necrosis and/or removal of tissue. There is a known time-temperature relationship in the thermal destruction of tissue accomplished by ablation. A threshold temperature for causing irreversible thermal damage to tissue is generally accepted to be about 41° Celsius (C). It is also known that the time required to achieve a particular level of cell necrosis decreases as the treatment temperature increases further above 41° C. It is understood that the exact time/temperature relationship varies by cell type, but that there is a general relationship across many cell types that can be used to determine a desired thermal dose level. This relationship is commonly referred to as an equivalent time at 43° C. expressed as:

$$t_{eq,43°\,C.} = \int R^{(T(t)-43°)} dt$$

where T is the tissue temperature and R is a unit-less indicator of therapeutic efficiency in a range between 0 and 5 (typically 2 for temperatures greater than or equal to 43° C., zero for temperatures below 41° C., and 4 for temperatures between 41 and 43° C.), as described in Sapareto S. A. and W. C. Dewey, *Int. J. Rad. Onc. Biol. Phys.* 10(6):787-800 (1984). This equation and parameter set represents just one example of the many known methods for computing a thermal dose, and any of methodology can be employed with the methods and devices of the present invention. Using equation (1) above, thermal doses in the range of $t_{eq,43°\,C.}$=20 minutes to 1 hour are generally accepted as therapeutic although there is some thought that the dose required to kill tissue is dependent on the type of tissue. Thus, therapeutic temperature may refer to any temperature in excess of 41° C., but the delivered dose and, ultimately, the therapeutic effect are determined by the temporal history of temperature (i.e., the amount of heating the tissue has previously endured), the type of tissue being heated, and equation (1). For example, Nath, S. and Haines, D. E., *Prog. Card. Dis.* 37(4):185-205 (1995) (Nath et al.) suggest a temperature of 50° C. for one minute as therapeutic, which is an equivalent time at 43° C. of 128 minutes with R=2. In addition, for maximum efficiency, the therapeutic temperature should be uniform throughout the tissue being treated so that the thermal dose is uniformly delivered.

Figure 3:
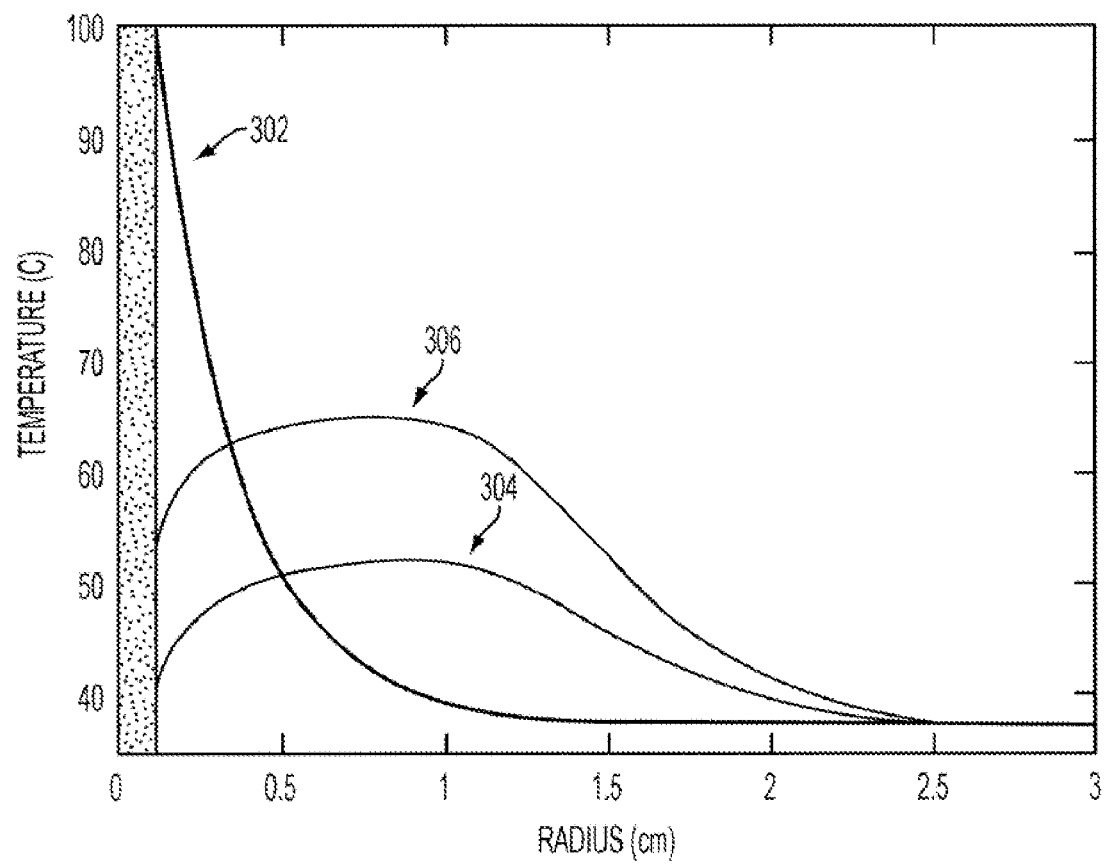
FIG. 3 is a graphical representation of simulated heating profiles for various forms of ablation.

FIG. 3 illustrates the performance profiles of several ablation techniques by showing a simulated temperature achieved at a given distance from an ablation element, such as electrode 105. The first profile 302 illustrates the performance of RF ablation without the use of fluid enhancement. As shown in the figure, the temperature of the tissue falls very sharply with distance from the electrode. This means that within 10 millimeters of the ablation element the temperature of the tissue is still approximately body temperature (37° C.), far below the therapeutic temperature of 50° C. discussed above. Furthermore, very close to the ablation element the temperature is very high, meaning that the tissue will more quickly desiccate, or dry up, and char. Once this happens, the impedance of the tissue rises dramatically, making it difficult to pass energy to tissue farther away from the ablation element.

A second tissue temperature profile 304 is associated with a second prior art system similar to that described in U.S. Pat. No. 5,431,649. In this second system, an electrode is inserted into tissue and imparts a 400 kHz RF current flow of about 525 mA to heat the tissue. Body temperature (37° C.) saline solution is simultaneously injected into the tissue at a rate of 10 ml/min. The resulting tissue temperature profile 304 is more uniform than profile 302, but the maximum temperature achieved anywhere is approximately 50° C. Thus, the temperature profile 304 exceeds the generally accepted tissue damaging temperature threshold specified for one minute of therapy in only a small portion of the tissue. As described above, such a small temperature increment requires significant treatment time to achieve any therapeutically meaningful results.

A third tissue temperature profile 306 is achieved using the teachings of the present invention. In the illustrated embodiment, an electrode formed from silver/silver chloride is inserted into tissue and imparts a 480 kHz RF current flow of 525 mA to heat the tissue. Saline solution heated to 50° C. is simultaneously injected into the tissue at a rate of 10 ml/min. The resulting temperature profile 306 is both uniform and significantly above the 50° C. therapeutic threshold out to 15 millimeters from the electrode. Moreover, because the temperature is uniform within this volume, the thermal dose delivered is also uniform through this volume.

The uniform temperature profile seen in FIG. 3 can be achieved by the introduction of heated fluid into the target tissue during application of ablative energy. The fluid convects the heat deeper into the tissue, thereby reducing the charring and impedance change in tissue that occurs near the ablation element, as shown in profile 302. Further, because the fluid is heated to a therapeutic level, it does not act as a heat sink that draws down the temperature of the surrounding tissue, as seen in profile 304. Therefore, the concurrent application of RF energy and perfusion of heated saline solution into the tissue eliminates the desiccation and/or vaporization of tissue adjacent to the electrode, maintains the effective tissue impedance, and increases the thermal transport within the tissue being heated with RF energy. The total volume of tissue that can be heated to therapeutic temperatures, e.g., greater than 41° C., is thereby increased. For example, experimental testing has demonstrated that a volume of tissue having a diameter of approximately 8 centimeters (i.e., a spherical volume of approximately 156 cm$^3$) can be treated in 5 minutes using the fluid enhanced ablation techniques described herein. By comparison, conventional RF can only treat volumes having a diameter of approximately 3 centimeters (i.e., a spherical volume of approximately 14 cm$^3$) in the same 5-minute time span.

In addition, fluid enhanced ablation devices according to the present invention have a greater number of parameters that can be varied to adjust the shape of the treatment profile according to the tissue being treated. For example, when using the SERF ablation technique, an operator or control system can modify parameters such as saline temperature (e.g., from about 40° C. to about 80° C.), saline flow rate (e.g., from about 0 ml/min to about 20 ml/min), RF signal power (e.g., from about 0 W to about 100 W), and duration of treatment (e.g., from about 0 minutes to about 10 minutes) to adjust the temperature profile 306. In addition, different electrode configurations can also be used to vary the treatment. For example, although the emitter electrode 105 illustrated in FIG. 1 is configured as a continuous cylindrical band adapted for a mono-polar current flow, the electrode can also be formed in other geometries, such as spherical or helical, that form a continuous surface area, or the electrode may have a plurality of discrete portions. The electrodes may also be configured for bipolar operation, in which one electrode (or a portion of an electrode) acts as a cathode and another electrode (or portion thereof) acts as an anode.

A preferred fluid for use in the SERF ablation technique is sterile normal saline solution (defined as a salt-containing solution). However, other liquids may be used, including Ringer's solution, or concentrated saline solution. A fluid can be selected to provide the desired therapeutic and physical properties when applied to the target tissue and a sterile fluid is recommended to guard against infection of the tissue.

Fluid Shaping of Therapy Zone

As mentioned above, ablative energy generally expands from an ablation element, such as emitter electrode 105, in a spherical pattern. This, in turn, creates ablation therapy treatment zones, volumes, or regions (i.e., regions that receive a therapeutic dose of ablative energy by reaching a therapeutic temperature for a period of time, as discussed above) that have a roughly spherical shape. The diameter of the spherical treatment zone can increase as the treatment time is lengthened.

Figure 4:
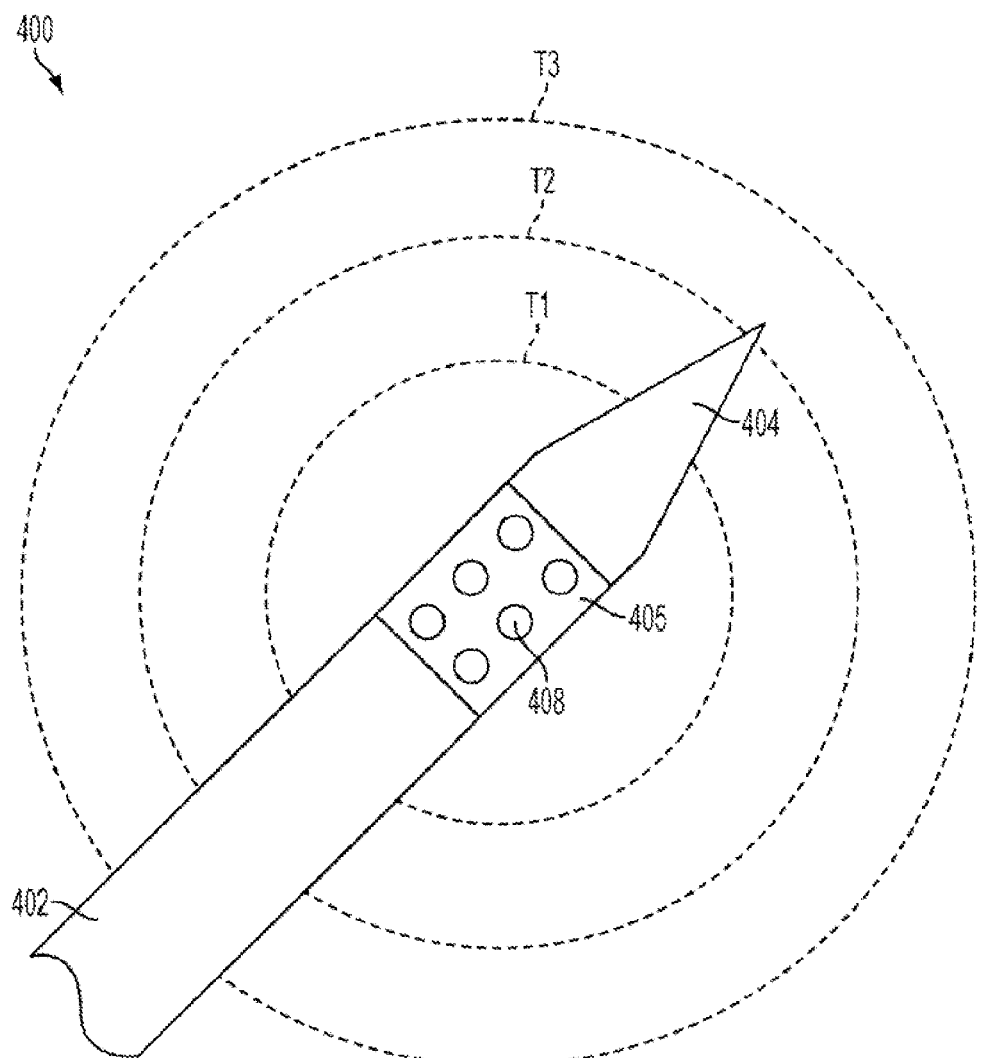
FIG. 4 is a side view of a distal portion of an elongate body showing the expansion of a treatment zone over time.

One embodiment of this behavior is illustrated in FIG. 4. The figure shows one embodiment of an ablation device 400 that includes an elongate body 402 having a distal tip 404 and an emitter electrode 405. A plurality of outlet ports 408 can be positioned along an outer surface of the emitter electrode 405 and can be configured to deliver fluid into the tissue surrounding the elongate body 402. As heated fluid is delivered from the outlet ports 408 and ablative energy is delivered into the tissue via the emitter electrode 405, a treatment zone develops at a first time that is defined by the dotted lines labeled $T_1$. While drawn as a two-dimensional circle, one skilled in the art will appreciate that the treatment zone represented is three-dimensional and is roughly spherical in shape. As the treatment time increases, so too does the diameter of the treatment zone, until it reaches the dotted lines labeled $T_2$ at a second time that is greater than the first time. Similarly, at a third time greater than the second time, the treatment zone can reach the dotted lines labeled $T_3$.

In certain situations, however, it can be desirable to provide a therapeutic dose of ablative energy to a volume of tissue that is not spherically shaped. For example, in some embodiments ablation may be used to treat a fibroid, tumor, or other lesion that is not symmetrically or spherically shaped. In other embodiments, the volume of tissue to be treated may be located very close to another tissue structure to be spared from treatment, such as a cluster of nerve cells or other healthy tissue. Still further, in some embodiments, it may be desirable to create a treatment region having a definite directionality (e.g., a plane of ablated tissue having a length and a thickness). An exemplary use for a directional treatment zone is the treatment of cardiac dysrhythmias (e.g., ventricular tachycardia) with ablation. In such a procedure, ablation can be used to create directional paths to guide the propagation of the electrical signals that control heartbeats, thereby preventing errant signals that can produce a tachycardia. These paths are commonly created as vertical planes in the walls of the heart.

The present invention provides devices and methods for producing these types of directional and otherwise non-spherical treatment regions during fluid enhanced ablation therapy. In general, the devices and methods of the present invention operate by using fluids of varying temperatures to shape the treatment region. In one embodiment, fluid heated to a therapeutic temperature can be introduced into tissue from an elongate body at one or more locations, and fluid at a lower temperature can be introduced from the same or a different elongate body at one or more different locations. In certain regions surrounding the one or more elongate bodies, the higher temperature fluid can mix with the lower temperature fluid, resulting in quenching (i.e., cooling of the heated fluid below a therapeutic temperature). This quenching can prevent the delivery of a therapeutic dose of ablative energy at a particular location. The relative placement of the fluid sources, as well as the selection of operating parameters such as flow rate and temperature, can provide greater control and customization of the treatment region created during fluid enhanced ablation therapy. A person skilled in the art will appreciate that the various methods and devices disclosed herein can be used to create treatment regions having any desired shape.

Multi-Body System

Figure 5:
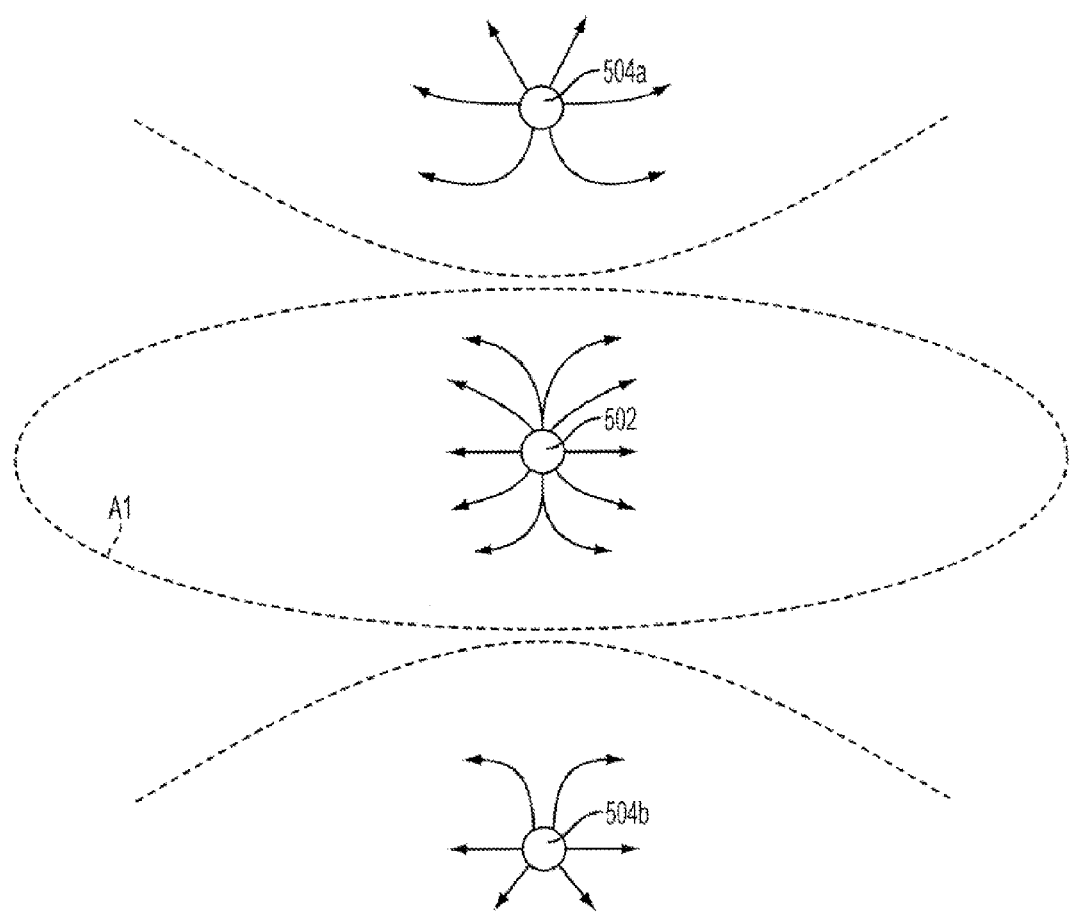
FIG. 5 is a cross-sectional schematic of a treatment zone that can be created by one embodiment of a fluid enhanced ablation system of the present invention.

FIG. 5 illustrates one embodiment of a system of the present invention. The figure depicts a top cross-sectional view (i.e., the elongate bodies discussed below extend through the page) of one embodiment of a fluid enhanced ablation system having multiple elongate bodies delivering fluid at varying temperatures. In particular, a first elongate body 502 can be positioned substantially in the center of a volume to be treated. The first elongate body 502 can be similar to the elongate body 102 discussed above. A second elongate body 504a and a third elongate body 504b can be positioned adjacent to the first elongate body 502 as shown. The second and third elongate bodies 504a, 504b can be similar to the elongate body 102 discussed above in some embodiments. In other embodiments, however, the second and third elongate bodies can lack one or more of the ablation element and the heating assembly of the elongate body 102, as these bodies are not used to deliver therapeutically heated fluid or ablative energy. In certain embodiments, a heating assembly may still be included in the second and third elongate bodies 504a, 504b to allow them to heat fluid flowing therethrough to an elevated temperature, e.g., a temperature below the therapeutic threshold but above body temperature (though any elevated temperature is possible).

In use, fluid from a first fluid source can be delivered into tissue surrounding the first elongate body 502 by passing the fluid through the inner lumen, heating the fluid, and ejecting the fluid through at least one outlet port formed in a sidewall of the elongate body 502, as discussed above. The heated fluid can be at a therapeutic temperature, for example, between about 45° C. and about 80° C. In one embodiment, the fluid can be heated to about 50° C. In addition, fluid of a second, lower temperature can be delivered from the same or different fluid sources into tissue surrounding the second and third elongate bodies 504a, 504b. The lower temperature fluid can be any temperature less than the temperature of the fluid delivered through the elongate body 502. In one embodiment, the lower temperature fluid can be between about 25° C. and about 41° C., though fluid of any temperature can be used so long as it quenches any thermal dose. The fluid flow from each of the first, second, and third elongate bodies 502, 504a, 504b is represented by arrows in FIG. 5. As mentioned above, the higher temperature fluid coming out of the first elongate body 502 can mix with the lower temperature fluids coming out of the second and third elongate bodies 504a, 504b to prevent certain areas of tissue from reaching the therapeutic temperature, thereby preventing tissue damage. This fluid interaction and resulting selective quenching of heat in the tissue can produce a treatment volume having an elliptical shape, as indicated by the dotted lines labeled $A_1$ in FIG. 5. One skilled in the art will appreciate that while the treatment region $A_1$ in FIG. 5 is shown as elliptical, the treatment volume extends in three dimensions and resembles an elliptical disk or a sphere that has been compressed from opposing sides by the fluid flows from the second and third elongate bodies 504a, 504b.

The configuration shown in FIG. 5 is one of a variety of possible configurations for the fluid enhanced ablation system disclosed herein. For example, in certain embodiments, more than one elongate body may be configured to deliver therapeutically heated fluid, or heated fluid as well as ablative energy. Similarly, more or less than the two elongate bodies 504a, 504b may be utilized to deliver fluid at a lower temperature to areas adjacent to the one or more elongate bodies used to ablate tissue. As a result, a number of different three-dimensional therapy zone shapes can be achieved using any number of elongate bodies supplying fluid to the tissue. Still further, the one or more elongate bodies can be positioned at a variety of locations with respect to one another. Variations can include angular adjustments (e.g., placing the third elongate body 504b to the left of the first elongate body 502 in the figure, rather than below), distance adjustments (e.g., moving the third elongate body 504b farther away from the first elongate body 502 in the figure), and vertical adjustments (e.g., moving the second elongate body 504a in a direction normal to the plane of the figure). In addition, a variety of temperatures may be selected for the fluids being delivered through any of the elongate bodies. In one embodiment, the fluid flowing through the first elongate body 502 can be heated to a therapeutic temperature. The fluids flowing through the second and third elongate bodies 504a, 504b can be heated to any temperature less than the therapeutic temperature. For example, the fluids can delivered at body temperature with no active heating, or the fluids can be delivered at a temperature below body temperature. Furthermore, the flow rates and temperatures of the fluids injected from the first, second, and third elongate bodies can be adjusted to produce different variations of the shape shown in FIG. 5. In addition, the ablative energy delivered from any ablation elements disposed on the elongate bodies can be varied, and any number of elongate bodies can be positioned in or around the treatment zone to produce the desired therapy.

Figure 6:
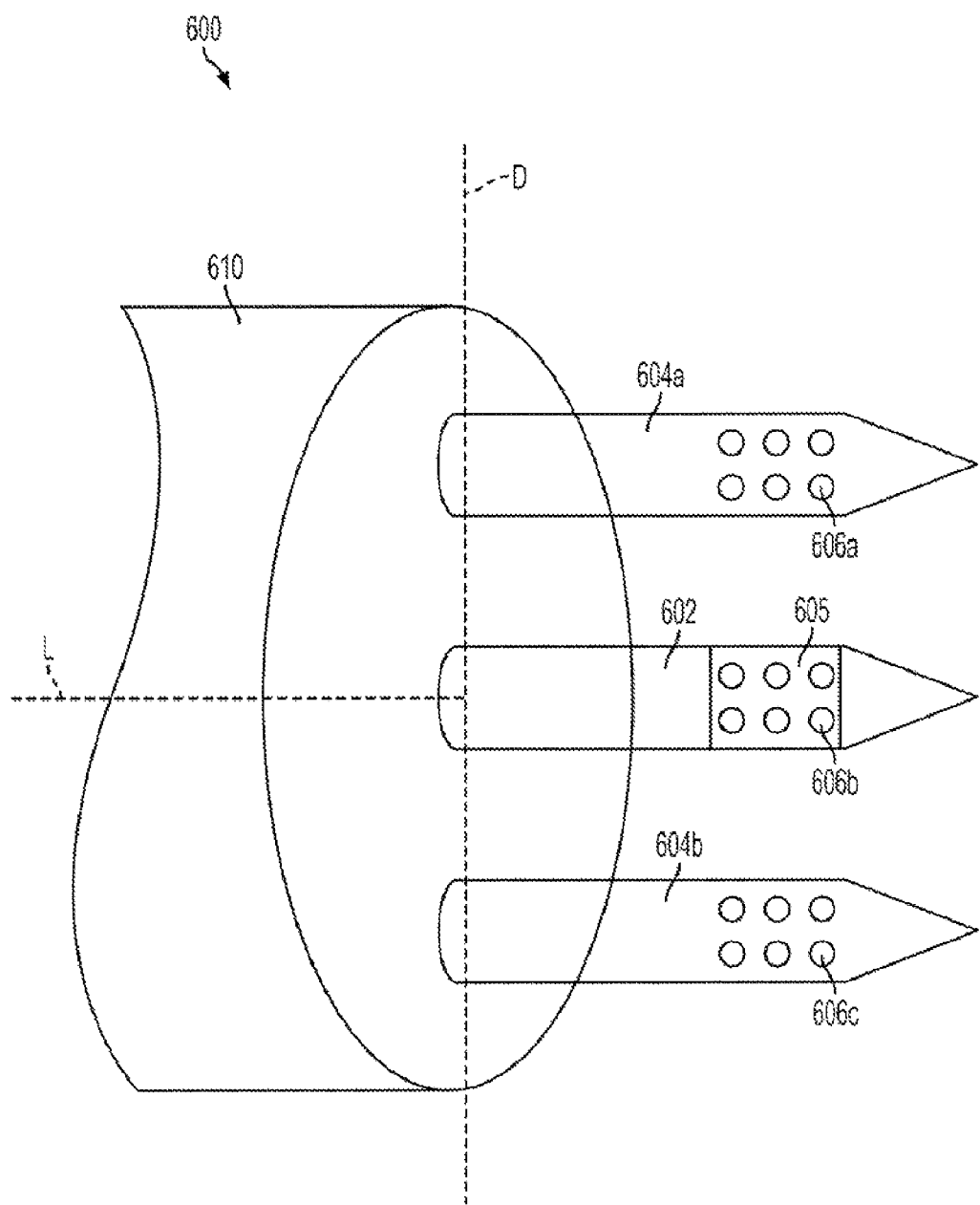
FIG. 6 is a perspective view of one embodiment of an ablation device having three elongate bodies extending longitudinally from a catheter.

The elongate bodies 502, 504a, 504b depicted in FIG. 5 can be introduced and positioned within a target volume of tissue in a variety of manners as well. For example, three separate devices similar to the medical device 200 discussed above can be utilized. In some embodiments, however, an ablation device can be provided having a plurality of elongate bodies affixed thereto where each elongate body can be coupled to the same or different fluid sources, as well as a heating assembly and an ablation element, if required. FIG. 6 illustrates one embodiment of such a device 600 that can include an elongate shaft 610, a first elongate body 602, a second elongate body 604a, and a third elongate body 604b. The first elongate body 602 can be configured to deliver fluid heated to a therapeutic temperature to surrounding tissue along with ablative energy from, for example, an emitter electrode 605. The second and third elongate bodies 604a, 604b can be configured to deliver fluid to the surrounding tissue at a lower temperature than the first elongate body 602. Additionally, each of the elongate bodies 602, 604a, 604b can have one or more outlet ports 606a, 606b, 606c configured to deliver fluid from the respective inner lumens of the elongate bodies 602, 604a, 604b into the surrounding tissue.

The elongate shaft 610 can have a variety of sizes and configurations. For example, in some embodiments the elongate shaft can be a catheter configured for entry into a patient's body via the circulatory system. In one exemplary embodiment, the catheter can be about 12 French. Each of the first, second, and third elongate bodies 602, 604a, 604b can be sized according to the overall diameter of the catheter used as the elongate shaft 610. In one exemplary embodiment, each of the elongate bodies can be a 27 gauge stainless steel needle body (i.e., having an outer diameter of about 0.4 mm). In another exemplary embodiment, the elongate shaft 610 can be configured as a laparoscopic device similar to the medical device 200 discussed above.

The elongate bodies 602, 604a, 604b can be positioned in a variety of configurations with respect to the elongate shaft 610. In the embodiment illustrated in FIG. 6, the elongate bodies 602, 604a, 604b can be evenly-spaced along an axis D that defines a diameter of the elongate shaft 610. More specifically, the first elongate body 502 can be positioned at a central portion of the elongate shaft 610, and the first elongate body 604a and the second elongate body 604b can be positioned along the axis D at an outer portion of the diameter of the elongate shaft. The elongate bodies 602, 604a, 604b can extend in a direction that is substantially parallel to a longitudinal axis L of the elongate shaft 610. In other embodiments, the elongate bodies 602, 604a, 604b, or at least the second and third elongate bodies 604a, 604b, can be configured to slide along the axis D to adjust the spacing between the elongate bodies 602, 604a, 604b. In still other embodiments, the elongate bodies 602, 604a, 604b can be angularly offset from each other at a particular radius from the longitudinal axis L. For example, the elongate bodies 602, 604a, 604b can be positioned every 120° at a distance from the longitudinal axis L. In such an embodiment, ablation elements can be provided on each of the elongate bodies 602, 604a, 604b and varying power levels, fluid flow rates, and fluid temperatures can be utilized to produce desired therapy zones.

As mentioned above, the first elongate body 602 can include an ablation element, such as the emitter electrode 605, configured to deliver RF energy to heat tissue surrounding the elongate body 602. In certain embodiments, the second and third elongate bodies 604a, 604b may include ablation elements as well (e.g., the ablation elements can be operated at very low power or remain inactive during therapy) or, in some embodiments, may not include ablation elements at all. Furthermore, each of the elongate bodies 602, 604a, 604b can include a heating assembly disposed within an inner lumen and configured to heat fluid flowing therethrough. The heating assemblies utilized can be similar to those discussed above and in related U.S. application Ser. No. 13/445,036 entitled "Methods and Devices for Remote Temperature Monitoring in Fluid Enhanced Ablation Therapy," filed concurrently with the present application and incorporated by reference in its entirety above. As mentioned above, the second and third elongate bodies 604a, 604b can, in some embodiments, not include a heating assembly, or an included heating assembly in each of the second and third elongate bodies can remain inactive if heating is not required or desired. Moreover, a person skilled in the art will appreciate that the elongate shaft can have any number of elongate bodies disposed thereon, and the elongate bodies can be oriented in a variety of angular directions with respect to the catheter.

Single-Body Devices

Effective shaping of the treatment zone created during fluid enhanced ablation therapy can also be accomplished using devices having only a single elongate body. For example, in one embodiment, an ablation device can include an elongate body with an inner lumen divided into two or more portions not in fluid communication with each other where each portion can be in communication with a common or separate fluid source and one or more different outlet ports positioned along the elongate body. Accordingly, fluid can be delivered to different areas surrounding the elongate body at a variety of temperatures. After exiting the one or more outlet ports, the fluid can mix, resulting in selective quenching of the heat building in certain areas of tissue surrounding the elongate body. This selective quenching can prevent tissue damage, thereby shaping the volume of tissue that receives a therapeutic dose of energy.

Figure 7A:
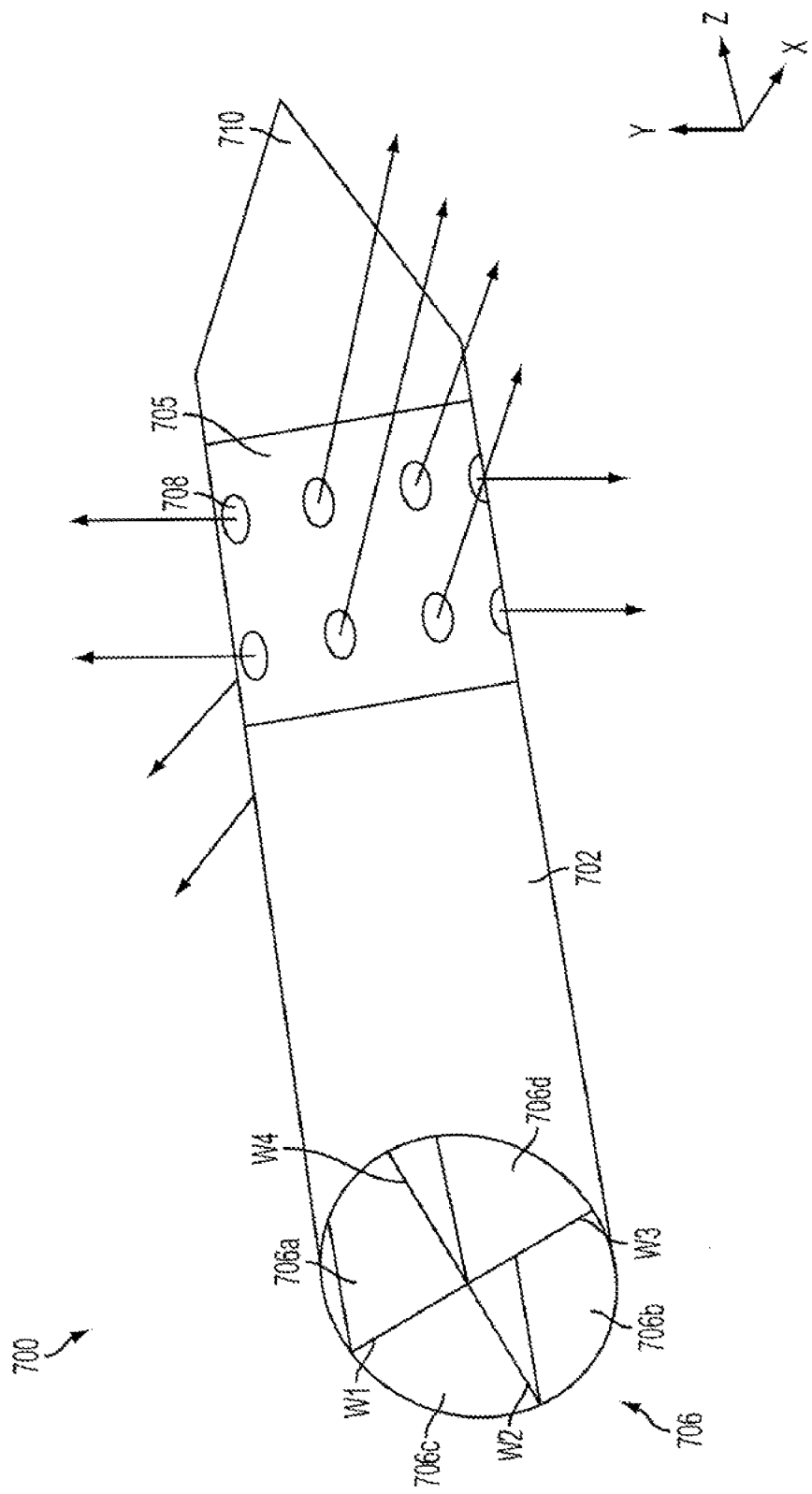
FIG. 7A is a perspective view of one embodiment of an ablation device that includes an elongate body having an inner lumen divided into portions extending longitudinally along the inner lumen.

FIG. 7A illustrates one embodiment of a single-body ablation device 700 that includes an elongate body 702 having an inner lumen 706 that is divided by a plurality of inner walls $w_1$, $w_2$, $w_3$, $w_4$ into a plurality of portions in the form of quadrants 706a, 706b, 706c, 706d. Each quadrant 706a, 706b, 706c, 706d therefore defines a separate inner lumen extending through the elongate body 702. A person skilled in the art will appreciate that inner lumens can be formed in the elongate body in other configurations, and that the elongate body can have any number of inner lumens. The device 700 can also include a pointed (or otherwise shaped) distal end 710, an ablation element (e.g., an emitter electrode) 705, and a plurality of outlet ports 708.

The inner walls $w_1$, $w_2$, $w_3$, $w_4$ can extend along the entire length of the elongate body 702 such that the quadrants 706a, 706b, 706c, 706d defined by the walls are not in fluid communication with each other. The interfaces between the inner walls $w_1$, $w_2$, $w_3$, $w_4$ and the inner wall of the elongate body 702 can include features, such as a sealant or adhesive, that prevent fluid from leaking between the quadrants 706a, 706b, 706c, 706d. Furthermore, the inner walls $w_1$, $w_2$, $w_3$, $w_4$ can be formed from or coated in a thermally and possibly electrically insulating material to prevent heated fluid in one quadrant from warming fluid in an adjacent quadrant. For example, the inner walls $w_1$, $w_2$, $w_3$, $w_4$ can be formed from or coated in the same fluoropolymer discussed above with respect to the elongate body 102. In some embodiments, thermal insulation may not be necessary. For example, a fast fluid flow rate (e.g., 10 ml/min or more) can reduce the amount of time fluid spends traveling through the inner lumen 706, thereby reducing the amount of heat transfer that can occur between adjacent quadrants.

Each of the quadrants 706a, 706b, 706c, 706d can be in fluid communication with one or more of the outlet ports 708. For example, in the embodiment illustrated in FIG. 7A, quadrant 706a of inner lumen 706 can be in fluid communication with one or more of the outlet ports 708 that direct fluid in a positive y direction. Conversely, quadrant 706b can be in fluid communication with one or more of the outlet ports 708 that direct fluid in a negative y direction. Similarly, quadrants 706c and 706d can be in fluid communication with one or more of the outlet ports 708 that direct fluid in a negative x direction and positive x direction, respectively. A person skilled in the art will appreciate that the quadrants 706a, 706b, 706c, 706d can each be in fluid communication with different outlet ports than those shown in FIG. 7A, and that any number of outlet ports can be positioned at various locations along the elongate body 702.

Figure 7B:
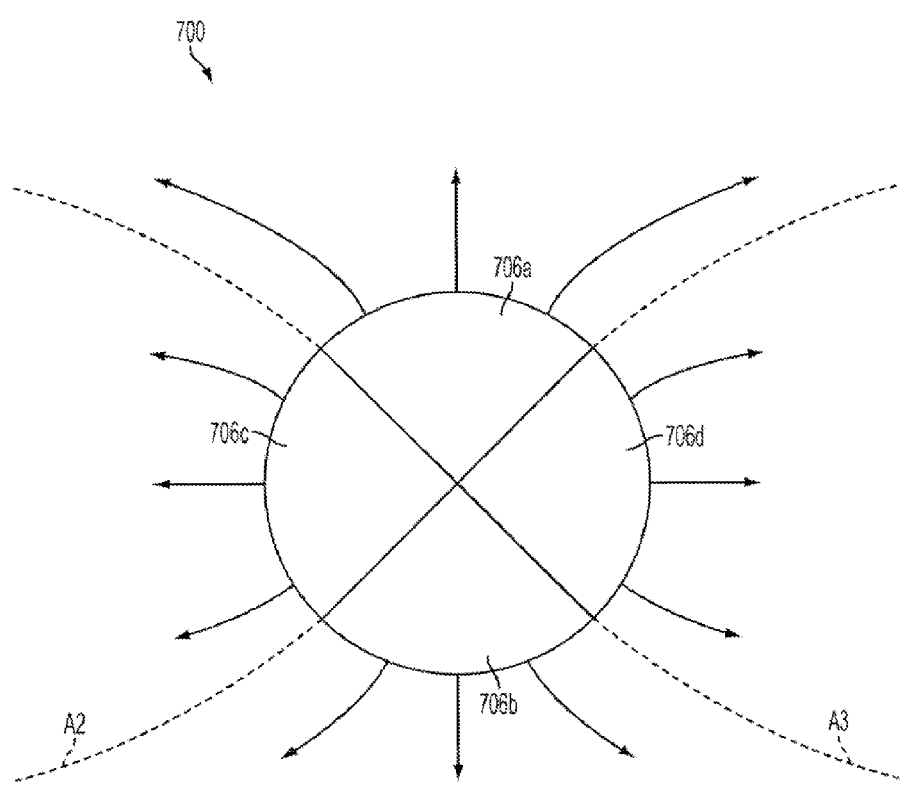
FIG. 7B is a cross-sectional view of the device of FIG. 7A depicting fluid flow with arrows and showing resulting treatment zones.

FIG. 7B illustrates the device of FIG. 7A in cross-section. As shown, fluid ejected from quadrants 706c and 706d of the inner lumen 706 can be heated to a therapeutic temperature by separate heating assemblies disposed within each quadrant (not shown). Fluid ejected from quadrants 706a and 706b, on the other hand, can be at a second temperature that is less than the therapeutic temperature of the fluid delivered from quadrants 706c and 706d. As described above, the second temperature can be less than body temperature, equal to body temperature, or greater than body temperature but less than the selected therapeutic temperature. Further, this second temperature can be achieved by delivering fluid at the second temperature or by utilizing separate heating assemblies (not shown) in the quadrants 706c, 706d to heat the fluid flowing therethrough to the second temperature. As the fluid from each quadrant enters tissue surrounding the elongate body 702, it can mix and form the thermal boundaries shown by the dotted lines. These boundaries can define treatment zones $A_2$ and $A_3$ in which a therapeutic temperature is reached for a period of time sufficient to deliver a therapeutic dose of ablative energy. Tissue outside zones $A_2$ and $A_3$ can be prevented from receiving the therapeutic dose of ablative energy by the cooler fluid being ejected from quadrants 706a and 706b. A person skilled in the art will appreciate that each of the quadrants 706a, 706b, 706c, 706d can eject fluid at different temperatures and flow rates to form a variety of differently shaped therapy zones.

Figure 8A:
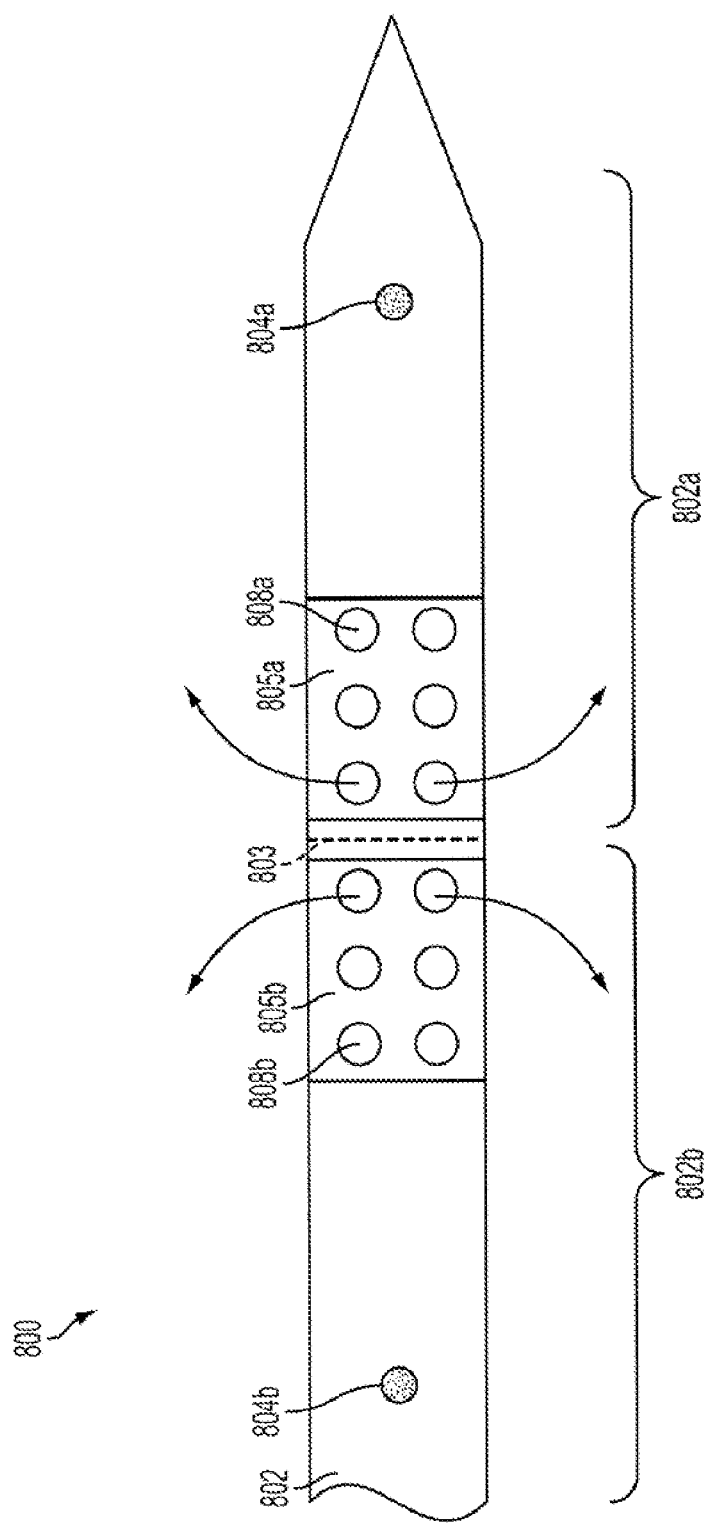
FIG. 8A is a side view of one embodiment of an elongate body having a plurality of ablation elements disposed along the elongate body.
Figure 8B:
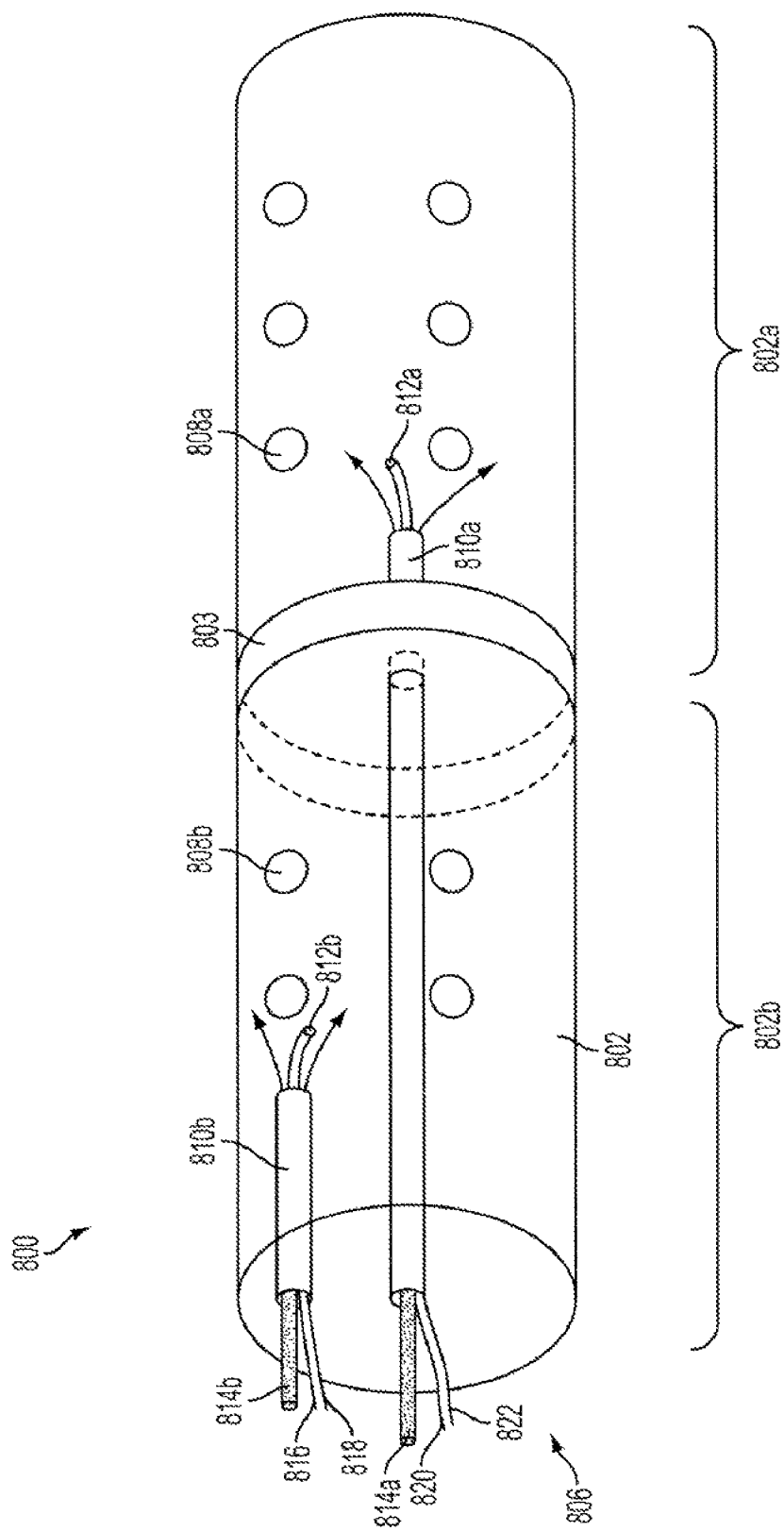
FIG. 8B is a perspective, semi-transparent view of the elongate body of FIG. 8A showing the division of the elongate body into proximal and distal portions that can each independently receive fluid at a given temperature.

FIGS. 8A and 8B illustrate another embodiment of a single-body ablation device 800 configured to deliver fluid at a variety of temperatures into a treatment volume. In contrast to the portions extending longitudinally through the inner lumen 706 in the device 700 depicted in FIGS. 7A and 7B, the device 800 can be divided into distal and proximal portions 802a, 802b. As shown in FIG. 8A, the ablation device 800 can include an elongate body 802 that is divided into a distal portion 802a and a proximal portion 802b by a baffling element 803. The baffling element 803 can be an inner wall that separates the inner lumen of the distal portion 802a of the elongate body from the inner lumen of the proximal portion 802b of the elongate body.

Each portion 802a, 802b can include an ablation element, such as an emitter electrode 805a, 805b, as well as one or more outlet ports 808a, 808b formed along the elongate body 802 and/or emitter electrode 805a, 805b that are in fluid communication with the inner lumen of each portion. The portions 802a, 802b can further include one or more temperature sensors 804a, 804b disposed along the elongate body and configured to detect the temperature of tissue surrounding the elongate body 802. The temperature sensors can be implemented in a variety of manners and, in some embodiments, the sensors can be fine-wire chromel-constantan thermocouples embedded in a hole formed in the sidewall of the elongate body 802. The temperature sensors 804a, 804b can be positioned at any location along the elongate body 802 but, in some embodiments, can be positioned symmetrically with respect to the ablation elements 805a, 805b. Such an arrangement can allow for a more accurate measurement of the uniformity of expansion of the treatment zone. More information regarding the temperature sensors can be found in related U.S. patent application Ser. No. 13/445,034 entitled "Methods and Devices for Remote Temperature Monitoring in Fluid Enhanced Ablation Therapy," filed concurrently with the present application and incorporated by reference above.

The division of the elongate body 802 into portions 802a, 802b can allow adjustment of the treatment zone in the event non-uniform heating is detected by the temperature sensors 804a, 804b. For example, the illustrated device can be particularly useful in the situation where fluid is delivered from both portions 802a, 802b at an equal temperature along with ablative energy from both electrodes 805a, 805b, but the temperature registered by temperature sensor 804a is greater than the temperature registered by sensor 804b. To adjust the therapy zone and provide more uniform heating, the delivery of ablative energy from electrode 805a can be reduced or stopped. In addition, the temperature of fluid being ejected from the one or more outlet ports 808a of distal portion 802a can be reduced. Furthermore, the fluid flow rate can be decreased if necessary. Each of these actions can reduce the heating taking place in the tissue surrounding distal portion 802a and help drive heated fluid being ejected from the outlet ports in proximal portion 802b toward the temperature sensor 804b and the tissue surrounding the elongate body 802 in that area. One skilled in the art will appreciate that the opposite steps (e.g., an increase in ablative energy, increase in saline temperature, etc.) can be applied to the portion 802a to increase the thermal dose delivered in that area. Furthermore, any of the steps recited above can be applied in reverse to provide more heating in the vicinity of the temperature sensor 804a should the observed conditions be reversed. Still further, the steps listed above can be performed in any order and may be performed individually or in concert depending on the amount of therapy shaping that is desired or required.

FIG. 8B illustrates a semi-transparent view of the device of FIG. 8A and shows the internal construction of one embodiment of an elongate body having proximal and distal portions separated by one or more baffling members 803. As shown, the inner lumen of distal portion 802a can be separated from proximal portion 802b by the baffling member 803. The baffling member 803 can be constructed similarly to the walls $w_1$, $w_2$, $w_3$, $w_4$ discussed above. For example, the baffling member can be an integrated portion of the elongate body 802, or can be a separate component secured in the inner lumen 806 of the elongate body 802 by an adhesive or other retaining component or material. The baffle 803 can be formed, for example, from a plastic or other suitable material.

The baffling element 803 can further include one or more lumens formed therein that are each configured to receive a cannula, such as cannula 810a. The cannula 810a can be formed from metal, plastic, or plastic having a metal lining, and can include an inner lumen that provides a fluid passageway to the proximal end of the device 800 through any intervening baffles (e.g., the baffle 803) and portions (e.g., the proximal portion 802b). The inner lumen of the cannula 810a is not in fluid communication with the inner lumen of any other portion (e.g., proximal portion 802b). This allows, for example, fluid to be delivered into distal portion 802a from a source that is separate from the source used to deliver fluid to proximal portion 802b. Alternatively, fluid can be delivered into both portions 802a, 802b from a common source. The inner lumen 806 can also include additional cannulas configured to deliver fluid to other portions of the device 800. For example, the inner lumen 806 can include a cannula 810b configured to deliver fluid from a proximal end of the device 800 into the proximal portion 802b of the distal end of the device 800.

One skilled in the art will appreciate that the inner lumen 806 can include as many cannulas as there are portions in the device. Further, the device 800 can have any number of portions depending on the desired shape of the treatment zone. For example, the device 800 can include two portions as illustrated in FIG. 8, or can have three or more portions. In an embodiment having three portions, for instance, a centrally-located ablation element can be bordered on each side by one or more outlets configured to deliver lower temperature fluid into the tissue surrounding the elongate body 802. In such an embodiment, the bordering outlets can compress the treatment zone along the direction of a longitudinal axis of the elongate body 802.

In addition, the cannulas can each be rigidly held in position by a spacer element (e.g., an element similar to the baffle 803 but also including one or more lumens to allow the passage of fluid around the baffle) or can be allowed to float in the inner lumen 806. In other embodiments, the cannulas can include features formed on an external surface thereof to prevent contact with other cannulas or the inner walls of the inner lumen 806. Exemplary features include fins or ribs formed on the outer surface of the cannulas.

Each cannula 810a, 810b can be connected at a proximal end to an independent or common fluid source. Each cannula 810a, 810b can also include an independent heating assembly disposed within the inner lumen of the cannula near its distal end. An exemplary heating assembly can include, for example, a single wire 814a, 814b running through the inner lumen of the cannula 810a, 810b that is configured to pass RF energy through fluid within the inner lumen of the cannula into the inner wall of the cannula. The wire 814a, 814b can include one or more spacers disposed thereon to prevent the wire from directly contacting the conductive portion of the cannula 810a, 810b. A more detailed description of such a heating assembly can be found in U.S. application Ser. No. 13/445,036 entitled "Methods and Devices for Remote Temperature Monitoring in Fluid Enhanced Ablation Therapy," filed concurrently with the present application and incorporated by reference above.

The exemplary heating assembly described above requires that each cannula 810a, 810b be at least partially formed from an electrically conductive material (to receive RF energy from the wire 814a, 814b). In such an embodiment, the cannulas 810a, 810b can be coated in an insulating material so as to prevent any electrical shorts due to contact with each other or the inner walls of the inner lumen 806 of the device 800. In addition, a thermally insulating material can also be used to coat the cannulas 810a, 810b to prevent the temperature of fluid in any one portion from influencing the temperature of fluid in other portions. However, in some embodiments, the fluid flow rate can be high enough that fluid does not spend enough time in any one portion to influence, or be influenced by, the temperature of fluid in that portion. In these embodiments, thermal insulation of the cannulas 810a, 810b is not necessary.

The cannulas 810a, 810b can also include a temperature sensor configured to provide feedback regarding the temperature of fluid being delivered to a portion of the device 800. For example, the cannula 810a can include a dual-wire thermocouple 812a configured to extend beyond the distal end of the cannula 810a such that the thermocouple can measure the temperature of fluid within the distal portion 802a after it exits the cannula and mixes within the inner lumen 806 before exiting into the surrounding tissue through the outlet ports 808a. The two thermocouple wires 820, 822 can extend through the inner lumen of the cannula 810a back to the proximal end of the device 810a. The wires can be connected to signal processing electronics as known in the art to determine the temperature of the fluid in the distal portion 802a. As shown in the figure, the second cannula 810b can also include a temperature sensor 812b, such as a dual-wire thermocouple formed from two wires 816, 818. The sensor 812b can similarly be configured to extend beyond the distal end of the cannula 810b into the proximal portion 802b such that the temperature measured by the sensor 812b represents the temperature of mixed fluid that is about to be delivered into surrounding tissue via outlet ports 808b. One skilled in the art will appreciate that a variety of temperature sensors can be employed in the devices of the present invention, including, for example, chromel-constantan fine-wire thermocouples.

Methods of Use

The teachings of the present invention can be utilized to produce a treatment zone having any desired shape. In general, this can be accomplished by introducing fluid from two or more locations along with therapeutic energy (e.g., from an ablation element or from heating the fluid alone). For example, in some embodiments, a method can include delivering ablative energy and heated fluid at one or more locations while simultaneously delivering lower temperature fluid at one or more different locations to produce the desired treatment zone shape. By way of further example, in certain situations, it can be desirable to provide a generally spherical treatment volume but to exclude a particular subset of the volume from receiving a therapeutic dose of ablative energy. When utilizing fluid enhanced ablation in the area of the prostate, for example, it can be desirable to protect the nearby bundle of nerves that control incontinence and erectile function. Using the teachings of the present invention, this can be accomplished by introducing an elongate body into tissue adjacent to the structure to be protected and delivering a fluid below a selected therapeutic temperature during therapy, while simultaneously delivering energy to tissue to be treated.

Figure 9:
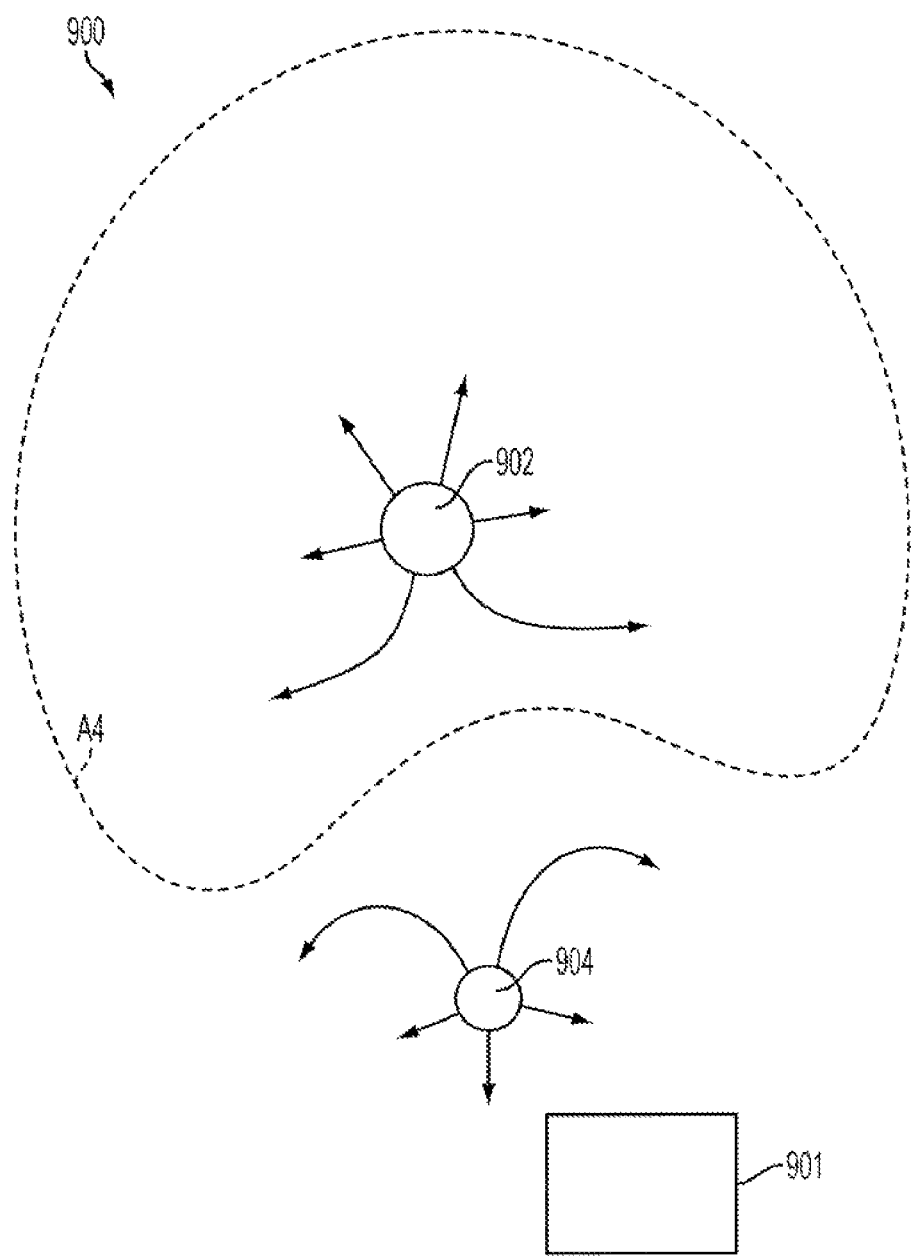
FIG. 9 is a cross-sectional view of one embodiment of a surgical site showing a tissue structure, a first elongate body delivering fluid at a first temperature, and a second elongate body delivering fluid at a second temperature to form a non-spherical treatment zone.

FIG. 9 illustrates a top cross-sectional view (similar to FIG. 5 above) of one embodiment of a non-spherical treatment zone. As shown in the figure, a first elongate body 902 is positioned substantially in the center of a treatment volume. The treatment volume, however, is located adjacent to a structure 901 (e.g., nerve bundle, healthy tissue, etc.) to be spared from the ablation therapy. To accomplish this, a second elongate body 904 can be positioned adjacent to the structure 901 and between the first elongate body 902 and the structure 901. During the fluid enhanced ablation therapy, in which the first elongate body delivers fluid heated to a therapeutic temperature along with RF energy into the surrounding tissue, the second elongate body 904 can deliver fluid into the surrounding tissue at a temperature below the therapeutic temperature. As discussed above, the fluids can mix in the surrounding tissue and reduce the temperature in the tissue surrounding the structure 901 below the therapeutic level. The resulting therapy treatment region is shown by the dotted lines labeled $A_4$. One skilled in the art will appreciate that this technique, as well as variations involving multiple ablative and non-ablative elongate bodies, can be used to protect a variety of tissue structures throughout the body.

In other embodiments, shaping of a treatment zone can be accomplished using a single elongate body configured to deliver fluid at multiple temperatures simultaneously. Such a device is described above and one exemplary treatment zone is illustrated in FIGS. 7A and 7B. Another embodiment of such a device is illustrated in FIGS. 8A and 8B. In use, any of these devices can be introduced laparoscopically or endoscopically into a patient's body and positioned adjacent to tissue to be treated. Fluid can then be delivered into the tissue to be treated through one or more inner lumens of the device. The fluid flowing through each inner lumen can be independently heated to a therapeutic temperature, or any temperature below the therapeutic temperature. Fluids at different temperatures can be delivered from different portions—along the length of the device or around its circumference—of the device to produce treatment zones of different shapes.

In still other embodiments, it can be desirable to shape a therapy treatment zone by introducing an elongate body configured to remove fluid from the surrounding tissue rather than deliver fluid into the tissue. Utilizing an elongate body configured to draw fluid from surrounding tissue can aid in developing a desired fluid flow pattern within a volume of tissue undergoing treatment. In some embodiments, withdrawing fluid may also be necessary when the treatment volume is unable to absorb and dissipate the quantities of fluid introduced during ablation therapy.

Figure 10:
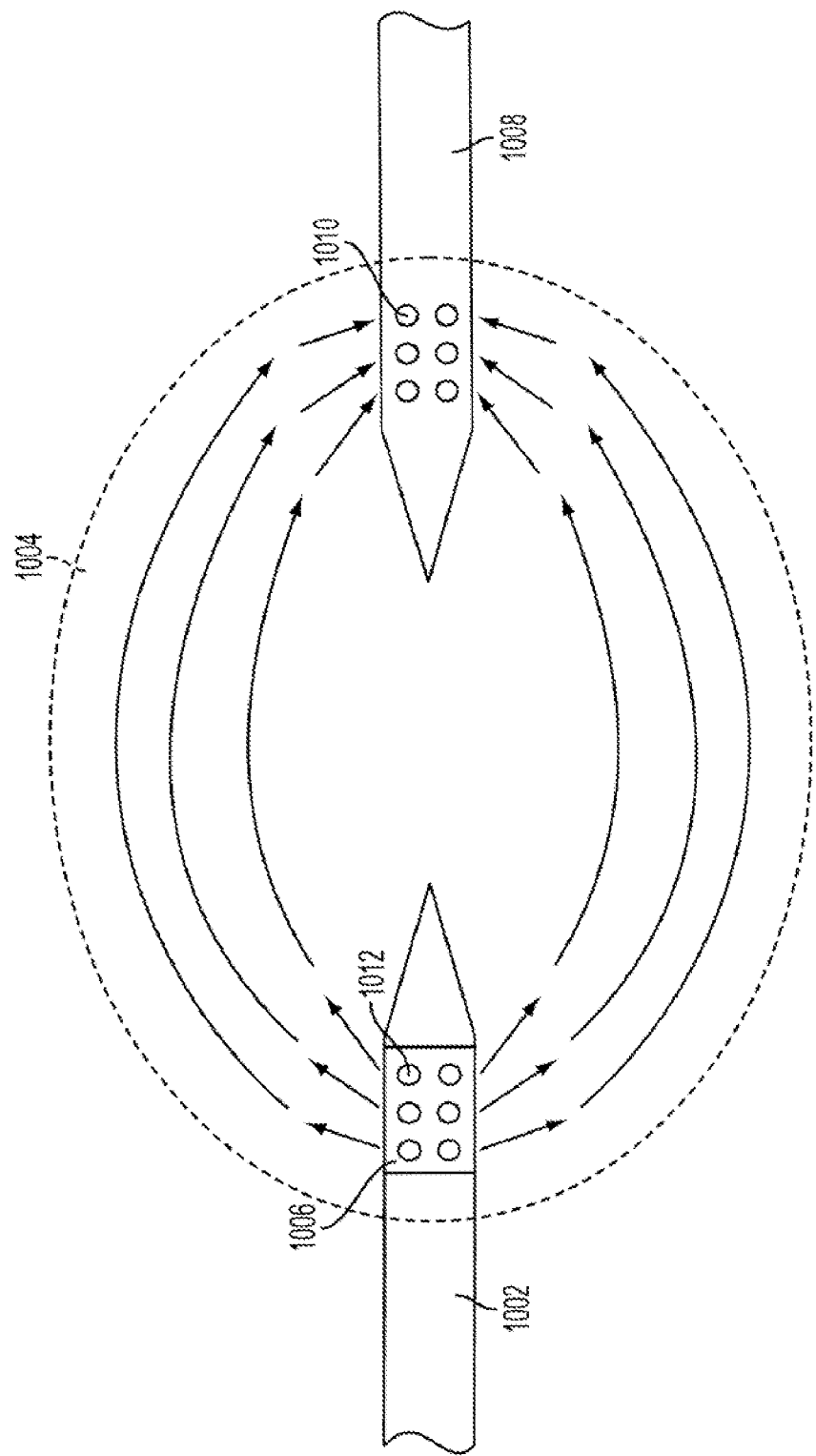
FIG. 10 is a cross-sectional view of one embodiment of a surgical site showing a first elongate body delivering fluid and therapeutic energy into a treatment zone and a second elongate body drawing fluid from the treatment zone.

FIG. 10 illustrates one embodiment of a method of delivering fluid enhanced ablation using one elongate body to deliver heated fluid and one elongate body to remove fluid from a treatment volume. As shown in the figure, a first elongate body 1002 can be inserted into a treatment volume 1004. Unlike the embodiments described above, however, the elongate body 1002 can be positioned such that the ablation element 1006 is located to one side of the treatment volume 1004, rather than being located substantially in the center of the treatment volume. A second elongate body 1008 can then be inserted into the treatment volume at a position substantially opposed to the first elongate body 1002. The second elongate body 1008 need not have an ablation element or, if it does, the ablation element can be deactivated. Further, the second elongate body 1008 can be configured to withdraw fluid from the surrounding tissue by, for example, connecting the inner lumen (that is in fluid communication with the surrounding tissue via one or more outlet ports 1010) of the second elongate body 1008 to a vacuum source.

After both the first and second elongate bodies 1002, 1008 are positioned within the treatment volume 1004, the first elongate body can begin delivering therapeutic energy from the ablation element 1006 as well as fluid heated to a therapeutic level from the one or more outlet ports 1012 formed in a sidewall of the elongate body 1002 or ablation element 1006. The second elongate body 1008 can also be activated to begin withdrawing fluid from the tissue in the treatment volume 1004. The simultaneous introduction and removal of fluid from the treatment volume can result in the development of a directional flow pattern between the first elongate body 1002 and the second elongate body 1008, as shown by the arrows in the figure.

One skilled in the art will appreciate that the technique of withdrawing fluid from a treatment area can be combined with any of the other techniques described herein to create a variety of complex therapy treatment zones having a number of shapes. Further, multiple elongate bodies configured to deliver ablative energy or withdraw fluid introduced into the treatment zone can be utilized concurrently. Still further, the placement of the first and second elongate bodies need not necessarily be opposed from one another, depending on the shape of the desired therapy region and the ability to access portions thereof. In fact, in some embodiments, the introduction and removal of fluid can be accomplished using a single elongate body, such as the device 800 shown in FIG. 8. In such an embodiment, one of the portions of the device can be configured to introduce fluid into a treatment volume, while another of the portions of the device can be configured to remove fluid from the volume.

The method illustrated in FIG. 10 can be particularly useful, for example, when treating encapsulated lesions, such as uterine fibroids. Encapsulated lesions have an outer coating that does not permit the passage of fluid, such as the fluid introduced during fluid enhanced ablation. As a result, if fluid is not withdrawn during therapy, the lesion can be undesirably stressed by the introduction of a significant volume of incompressible fluid. In addition, by positioning the first and second elongate bodies 1002, 1008 as shown in the figure, a strong directionality (as shown by the arrows) can be imposed on the propagation of the heat being delivered by the first elongate body 1002. Accordingly, therapy completion can be determined by measuring the temperature of the tissue surrounding the second elongate body 1008 using, for example, the same types of temperature sensors discussed above.

The various embodiments of the devices and systems disclosed herein can be utilized in a variety of surgical procedures to treat a number of medical conditions. For example, medical devices as disclosed herein can be configured for insertion into a target volume of tissue directly during an open surgical procedure. Alternatively, the medical devices can be configured to be passed through one or more layers of tissue during a laparoscopic or other minimally invasive procedure. Furthermore, the devices can be configured for introduction into a patient via an access port or other opening formed through one or more layers of tissue, or via a natural orifice (i.e., endoscopically). Following delivery to a treatment site, a portion of a surgical device, e.g., a distal portion of the elongate body 102, can be inserted into a target treatment volume such that an ablation element is disposed within the treatment volume. In some embodiments, the ablation element can be positioned near the center of the treatment volume.

Once the devices are positioned within the treatment volume, ablative energy and fluid heated to a therapeutic temperature can be delivered through one or more of the devices into the treatment volume. In addition, one or more other devices can deliver fluid at a lower temperature or withdraw fluid from the treatment volume. After a period of time, or depending on one or more feedback indications (e.g., a reading from a temperature sensor disposed within the treatment volume), the delivery of ablative energy and fluid can be stopped. The devices can then be removed and/or repositioned if additional therapy is required.

In addition, a large treatment zone having a first shape can be created by connecting several smaller treatment zones having a second shape. For example, a large linear treatment zone can be created by applying therapy that creates a slice-like shape (e.g., as shown in FIG. 5) and repositioning the device such that the ends of subsequent treatment zones overlap. A variety of other shapes can also be created using a similar method of connecting smaller treatment zones of a given shape and size.

Sterilization and Reuse

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present invention.

For example, the surgical devices disclosed herein may be disassembled partially or completely. In particular, the elongate body 202 of the medical device 200 shown in FIG. 2 may be removed from the handle 204, or the entire handle and elongate body assembly may be decoupled from the electrical and fluid connections 206, 208. In yet another embodiment, the handle, elongate body, and connections may be removably coupled to a housing that contains, for example, the fluid reservoir, pump, and power supply and controller shown in FIG. 1.

Preferably, the devices described herein will be processed before surgery. First, a new or used instrument can be obtained and, if necessary, cleaned. The instrument can then be sterilized. In one sterilization technique, the instrument is placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility.

In many embodiments, it is preferred that the device is sterilized. This can be done by any number of ways known to those skilled in the art including beta or gamma radiation, ethylene oxide, steam, and a liquid bath (e.g., cold soak). In certain embodiments, the materials selected for use in forming components such as the elongate body may not be able to withstand certain forms of sterilization, such as gamma radiation. In such a case, suitable alternative forms of sterilization can be used, such as ethylene oxide.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for forming an ablation treatment volume in tissue having a desired shape, comprising:
   positioning an ablation device having an elongate shaft and three elongate bodies extending from a distal end of the elongate shaft such that the three elongate bodies extend into tissue;
   delivering therapeutic energy to the tissue from only a first of the three elongate bodies to form an ablation treatment volume in the tissue; and
   simultaneously delivering a first fluid from the first elongate body and a second fluid from the other two elongate bodies to the tissue, the first and second fluids convecting the therapeutic energy in a desired direction such that the ablation treatment volume has a desired non-spherical shape;
   wherein each of the plurality of elongate bodies is offset from one another and spaced along an axis that defines a diameter of the elongate shaft with the first elongate body disposed between the other two elongate bodies.

2. The method of claim 1, wherein the first and second fluids are delivered at different temperatures.

3. The method of claim 2, further comprising heating at least one of the first fluid and the second fluid using a heating assembly disposed within an inner lumen of at least one of the three elongate bodies.

4. The method of claim 3, wherein the first fluid is heated using a first heating assembly disposed within a first inner lumen of the first elongate body to a temperature in excess of 41° C.

5. The method of claim 4, wherein the second fluid is heated to a temperature below 41° C.

6. The method of claim 1, further comprising adjusting any of a fluid flow rate and a fluid temperature for any of the first fluid and the second fluid to further shape the ablation treatment volume.

7. The method of claim 1, further comprising adjusting a level of therapeutic energy delivered to the tissue to further shape the ablation treatment volume.

8. The method of claim 1, wherein delivering therapeutic energy to tissue comprises activating an ablation element configured to transmit electrical energy into the tissue.

9. The method of claim 8, wherein the ablation element is disposed on the first elongate body.

10. The method of claim 1, further comprising repeating the steps of delivering therapeutic energy and simultaneously delivering a first fluid and a second fluid in a plurality of locations to form a treatment volume having an elongate planar shape.

11. The method of claim 1, wherein the second fluid is delivered from only a second of the three elongate bodies and the method further comprises delivering a third fluid from a third of the three elongate bodies simultaneously with delivering the first and second fluids.

12. The method of claim 1, wherein the elongate shaft is a catheter and positioning the ablation device includes introducing the elongate shaft into a patient's body via the circulatory system.

13. The method of claim 1, wherein simultaneously delivering each of the first and second fluids includes passing fluid from an inner lumen of each elongate body into tissue through at least one outlet port formed in each elongate body.

14. A method for shaping therapeutic energy delivered to tissue comprising:
   positioning an ablation device relative to tissue, wherein the ablation device includes an elongate shaft having:
      a first elongate body centrally disposed on and extending from a distal end of the elongate shaft, the first elongate body having an inner lumen extending therethrough, at least one outlet port formed therein, at least one ablation element disposed along a length thereof, and at least one heater element disposed within the inner lumen;
      a second elongate body extending from the distal end of the elongate shaft and offset from the first elongate body along an axis that defines a diameter of the elongate shaft, the second elongate body having an inner lumen extending therethrough and at least one outlet port formed therein;
      a third elongate body extending from the distal end of the elongate shaft and offset from the first elongate body along the axis in a direction opposite of the second elongate body offset, the third elongate body having an inner lumen extending therethrough and at least one outlet port formed therein; and simultaneously delivering a first fluid from the first elongate body and a second fluid from the second and third elongate bodies such that the first and second fluids interact to shape a non-spherical ablation treatment volume.

15. The method of claim 14, wherein the first fluid and the second fluid are at different temperatures.

16. The method of claim 14, further comprising delivering therapeutic energy from the ablation element disposed along the first elongate body.

17. The method of claim 14, wherein any of the second elongate body and the third elongate body is positioned at a location adjacent to a structure to be protected from therapeutic energy.

18. A method for forming an ablation treatment volume in tissue having a desired shape, comprising:

delivering therapeutic energy to tissue to form an ablation treatment volume in the tissue; and simultaneously delivering a first fluid and a second fluid to the tissue, the first and second fluids convecting the therapeutic energy in a desired direction such that the ablation treatment volume has a desired shape;

wherein the first fluid is delivered from first and second opposed longitudinal portions of an inner lumen of an elongate body, and the second fluid is delivered from third and fourth opposed longitudinal portions of the inner lumen, the third and fourth portions being radially offset from the first and second portions.

19. A method for forming an ablation treatment volume in tissue having a desired shape, comprising:

delivering therapeutic energy to tissue to form an ablation treatment volume in the tissue; and simultaneously delivering a first fluid and a second fluid to the tissue, the first and second fluids convecting the therapeutic energy in a desired direction such that the ablation treatment volume has a desired shape;

wherein delivering the first fluid comprises ejecting the first fluid from at least one outlet port formed in a proximal portion of a sidewall of an elongate member, and delivering the second fluid comprises ejecting the second fluid from at least one outlet port formed in a distal portion of a sidewall of an elongate member adjacent to the proximal portion.

* * * * *